(12) United States Patent
Maurer et al.

(10) Patent No.: US 9,983,204 B2
(45) Date of Patent: May 29, 2018

(54) MICROARRAY HAVING A BASE CLEAVABLE LINKER

(75) Inventors: Karl Maurer, Snohomish, WA (US); Dominic Suciu, Edmonds, WA (US); Hetian Gao, Fremont, CA (US)

(73) Assignee: CustomArray, Inc., Bothwell, WA (US)

( * ) Notice: Subject to any disclaimer, the term of this patent is extended or adjusted under 35 U.S.C. 154(b) by 1299 days.

(21) Appl. No.: 12/387,115

(22) Filed: Apr. 27, 2009

(65) Prior Publication Data

US 2009/0280998 A1    Nov. 12, 2009

Related U.S. Application Data

(63) Continuation of application No. 11/229,757, filed on Sep. 19, 2005, now abandoned, and a continuation of application No. 11/361,160, filed on Feb. 24, 2006, now Pat. No. 7,541,314.

(51) Int. Cl.
| | |
|---|---|
| C40B 50/18 | (2006.01) |
| G01N 33/543 | (2006.01) |
| B01J 19/00 | (2006.01) |
| C12Q 1/68 | (2018.01) |

(52) U.S. Cl.
CPC .... *G01N 33/54353* (2013.01); *B01J 19/0046* (2013.01); *C12Q 1/6837* (2013.01); *C40B 50/18* (2013.01); *B01J 2219/00454* (2013.01); *B01J 2219/00608* (2013.01); *B01J 2219/00653* (2013.01); *B01J 2219/00713* (2013.01); *B01J 2219/00722* (2013.01)

(58) Field of Classification Search
None
See application file for complete search history.

(56) References Cited

U.S. PATENT DOCUMENTS

| | | | |
|---|---|---|---|
| 3,950,357 A | 4/1976 | Kahan et al. | |
| 4,165,320 A | 8/1979 | Ondetti et al. | |
| 4,563,263 A | 1/1986 | Oyama et al. | |
| 4,840,893 A | 6/1989 | Hill | |
| 5,143,854 A * | 9/1992 | Pirrung et al. | 436/518 |
| 5,445,934 A | 8/1995 | Fodor et al. | |
| 5,510,270 A | 4/1996 | Fodor | |
| 5,540,828 A | 7/1996 | Yacynych | |
| 5,653,939 A | 8/1997 | Hollis et al. | |
| 5,667,667 A | 9/1997 | Southern | |
| 5,912,339 A | 6/1999 | Miller et al. | |
| 5,929,208 A | 7/1999 | Heller et al. | |
| 5,953,681 A | 9/1999 | Cantatore et al. | |
| 6,051,380 A | 4/2000 | Sosnowski | |
| 6,066,448 A | 5/2000 | Wohlstader | |
| 6,093,302 A | 7/2000 | Montgomery | |
| 6,280,595 B1 * | 8/2001 | Montgomery | 205/122 |
| 6,444,111 B1 | 9/2002 | Montgomery | |
| 6,456,942 B1 | 9/2002 | Anderson et al. | |
| 6,475,699 B2 | 11/2002 | Uetani et al. | |
| 6,518,024 B2 | 2/2003 | Choong et al. | |
| 6,576,426 B2 | 6/2003 | Southern et al. | |
| 6,743,564 B2 | 6/2004 | Hatakeyama et al. | |
| 6,780,582 B1 | 8/2004 | Wagner et al. | |
| 6,960,298 B2 | 11/2005 | Krotz et al. | |
| 7,008,769 B2 | 3/2006 | Henderson et al. | |
| 7,541,314 B2 * | 6/2009 | Suciu et al. | 506/13 |
| 9,339,782 B1 | 5/2016 | Gindilis | |
| 2002/0090738 A1 | 7/2002 | Cozzette | |
| 2002/0172963 A1 | 11/2002 | Kelley | |
| 2003/0050437 A1 | 3/2003 | Montgomery | |
| 2003/0111356 A1 | 6/2003 | Strathmann | |
| 2003/0113713 A1 | 6/2003 | Glezer | |
| 2003/0134989 A1 | 7/2003 | Aldrich et al. | |
| 2003/0190632 A1 | 10/2003 | Sosnowski | |
| 2003/0194709 A1 | 10/2003 | Yang | |
| 2004/0073017 A1 | 4/2004 | Skrzypcznski et al. | |
| 2005/0043894 A1 | 2/2005 | Fernandez | |
| 2005/0212902 A1 | 9/2005 | Cook | |
| 2005/0239112 A1 | 10/2005 | Padmanabhan | |
| 2005/0272088 A1 * | 12/2005 | Cook et al. | 435/6 |
| 2006/0102471 A1 | 5/2006 | Maurer | |
| 2006/0105355 A1 | 5/2006 | Maurer | |
| 2006/0160100 A1 | 7/2006 | Gao et al. | |
| 2006/0231411 A1 | 10/2006 | Maurer et al. | |
| 2007/0065877 A1 | 3/2007 | Maurer | |

(Continued)

FOREIGN PATENT DOCUMENTS

| | | |
|---|---|---|
| EP | 1420252 | 5/2004 |
| JP | 2005166601 | 6/2006 |

(Continued)

OTHER PUBLICATIONS

Verheijen et al (1999 Bioorganic & Medicinal Chemistry 7: 449-55).*
Pon et al (2004 Nucleic Acids Research 32:623-31).*
Afshari et al., "Application of Complementary DNA Microarray Technology to Carcinogen Identification . . . ", Cancer Res., 1999, pp. 4759-4760, vol. 59.
Bard et al., "Azo, Azoxy and Diazo Compounds," Encyclo. of Electrochemistry of the Elements, 1979, pp. 179-209-8, vol. XIII-4, NY, NY.
Beier et al., "Versatile Derivatisation of Solid Support Media for Convalent Bonding . . . " Nucleic Acids Research, 1999, pp. 1970-1977, vol. 27, No. 9.
Cahill et al., "Protein Arrays and their role in proteomics", Adv. Biochem. Engin/Biotechnol., 2003 pp. 177-187, vol. 83.
Campbell et al., "Enzyme-Amplified Amperometric Sandwich Test for RNA and DNA" Anal. Chem., 2002, 158-162, 74(1) American Chemical Society.

(Continued)

*Primary Examiner* — Christopher M Gross
(74) *Attorney, Agent, or Firm* — Sci-Law Strategies, PC

(57) ABSTRACT

There is disclosed a microarray having base cleavable linkers and a process of making the microarray. The microarray has a solid surface with known locations, each having reactive hydroxyl groups. The density of the known locations is greater than approximately 100 locations per square centimeter. Optionally, oligomers are synthesized in situ onto the cleavable linkers and subsequently cleaved using a cleaving base. Optionally, the oligomers are cleaved and recovered as a pool of oligomers.

21 Claims, 8 Drawing Sheets

(56) References Cited

U.S. PATENT DOCUMENTS

| | | |
|---|---|---|
| 2007/0072169 A1 | 3/2007 | Peyvan |
| 2007/0231794 A1 | 10/2007 | Dill et al. |
| 2007/0292855 A1 | 12/2007 | Dubin |
| 2008/0035494 A1 | 2/2008 | Gomez et al. |
| 2008/0039342 A1 | 2/2008 | Tian |
| 2008/0125327 A1 | 5/2008 | Kumar |
| 2011/0281766 A1 | 11/2011 | Cooper |

FOREIGN PATENT DOCUMENTS

| | | |
|---|---|---|
| WO | WO9603417 | 2/1996 |
| WO | WO0051721 | 9/2000 |
| WO | WO0123082 | 4/2001 |
| WO | WO0231463 | 4/2002 |
| WO | WO0231481 | 4/2002 |
| WO | WO02090963 | 11/2002 |
| WO | WO02103061 | 12/2002 |
| WO | WO03020415 | 3/2003 |
| WO | WO04024886 | 3/2004 |
| WO | WO2006055810 | 5/2006 |

OTHER PUBLICATIONS

Dill et al., "Antigen Detection Using Microelectrode Array Microchips" Analytica Chimica Acta, 2001, pp. 69-78, vol. 444.

Dill et al., "Immunoassays and Sequence-Specific DNA Detection on a Microchip . . . " J. Biochem. Biophys. Methods, 2004, 59 pp. 181-187, Elsevier B.V.

Drummond et al., "Electrochemical DNA Sensors" Nature Biotechnology Oct. 2003, 1192-1199, vol. 21, No. 10 Nature Publishing Group.

Egeland et al., "An Electrochemical Redox Couple Activitated by Microelectrodes for Confined Chemical Patterning of Surfaces" Analytical Chemistry (2002) vol. 74, pp. 1590-1596.

Fledler et al., "Diffusional Electrotitration: Generation of pH Gradients . . . " Analytical Chemistry, Mar. 1, 1995, pp. 820-828, vol. 67, No. 5.

Fodor et al., "Light-Directed, Spatially Addressable Parallel Chemical Synthesis" Science, Feb. 15, 1991, 767-773, vol. 251.

Gao et al., "In Situ Synthesis of Oligonucleotide Microarrays" Biopolymers Mar. 2004, pp. 579-596, vol. 73.

Ghindilis et al., "Immunosensors: Electrochemical Sensing and Other . . . " Biosensors & Bioelectronics 1998, pp. 113-131, vol. 13, No. 1, Elsevier Sciences S.A.

Greene et al., "Protective Groups in Organic Synthesis" Third Edition, Wiley-lnterscience, 1999.

Guo, et al., "Direct Fluorescence Analysis of Genetic Polymorphisms by Hybridization with Oligonucleotide . . . " Nucl. Acids Res., 1994, pp. 5456-5465, vol. 22, No. 24.

Hacia "Resequencing and mutational analysis using oligonucleotide microarrays" Nature Genetics 21 Supp.: 42, (1999).

Hacia et al., "Applications of DNA Chips for Genomic Analysis" Mol. Psychiatry, Nov. 1998, pp. 483-492, vol. 3, No. 6.

Hammerich et al., "Organic Electrochemistry, an Introduction & Guide" ed. by Lund and Baizer, 3rd Edition, 1991 pp. 615-657 Marcel Dekker, Inc., NY.

Johnston, "Gene Chips: Array of Hope for Understanding Gene Regulation" Curr. Biology, Feb. 26, 1998, R171-R174, vol. 8.

Krotz et al., "Large-Scale Synthesis of Antisense Oligonucleotides Without Chlorinated Solvents" Organic Process Res & Dev, 2000, pp. 190-193, vol. 4.

Kurian et al., "DNA Chip Technology" J. Pathology, 1999, pp. 267-271, vol. 187.

Lane et al., "Electrochemistry of Chemisorbed Molecules . . . " J. Physical Chemistry, 1973, pp. 1411-1421, vol. 77, No. 11 ($1^{st}$ Page Only).

Leproust et al., "Characterization of Oligodeoxyribonucleotide Synthesis on Glass Plates" Nucl. Acids Res., 2001, pp. 2171-2180, vol. 29, No. 10.

Maskos and Southern, "Oligodeoxyribonucleotide Synthesis on Glass Plates", Nucl. Acids Res., 1992, pp. 1679-1684, vol. 20.

Moller et al.. "Anodic oxidation of cyclohexene: Dependence of the product distribution on the reaction variables" Electrochimica Acta, vol. 42, No. 13, Jan. 1, 1997, pp. 1971-1978.

Ono et al., "Nucleosides and Nucleotides. 121. Synthesis of Oligonucleotides . . . " Bioconjugate Chem. 1993, pp. 499-508, vol. 4.

Patolsky et al. "Highly Sensitive Amplified Electronic Detection of DNA . . . " Chem. Eur. J., 2003, pp. 1137-1145, vol. 9, No. 5 Wiley-VCH Weinheim.

Patolsky et al., "Enzyme-Linked Amplified Electrochemical Sensing . . . " Langmuir 1999, vol. 15, No. 1,1 pp. 3703-3706, Am. Chemical Society.

Paul et al., "Acid Binding and Detritylation During Oligonucleotide Synthesis" Nucleic Acids Research, 1996, 3048-3052, vol. 24, No. 15.

Pellois et al., "Peptide Synthesis Based on t-Boc Chemistry & Solution Photogenerated Acids" J. Comb. Chem. 2000, pp. 355-360, vol. 2, No. 4.

Pillai, "Photoremovable Protecting Groups in Organic Chemistry" Synthesis 1980, pp. 1-26, vol. 39.

Ronlan, A. and Parker, V. D., "Anodic oxidation of phenolic compounds. Part II. Products and mechanisms of the anodic oxidation of hindered phenols" J. Chem. Soc. (C), 1971, pp. 3214-3218.

Rossier et al., "Enzyme Linked lmmunsorbent Assay on a Microchip . . . " Lab on a Chip 2001, vol. 1, pp. 153-157, The Royal Society of Chemistry.

Septak, M. "Kinetic Studies on Depurination and Detritylation of CPG-bound Intermediates . . . " Nucleic Acids Research, 1996, pp. 3053-3058, vol. 24, No. 15.

Shchepinov, M.S., "Oligonucleotide Dendrimers: From Poly-Labeled DNAc617 Probes to Stable Nano-Structures" Glen Report, Dec. 1999, vol. 12, No. 1.

Shchepinov et al., "Steric Factors Influencing Hybridisation of Nucleic Acids to Oligonucleotide Arrays" Nucl., Acids Res., 1997, pp. 115-1161, vol. 25, No. 6.

Soriaga et al., "Determination of Orientation of Adsorbed Molecules . . . ", J. Am. Chem. Soc., 1982, pp. 3937-3945, vol. 104 ($1^{st}$ Page Only).

Wang, G. et al., "Synthesis of Oligonucleotides Containing . . . " Tetrahedron Letters, 1993, 6721-6724, vol. 34, No. 42, Great Britain.

Wang et al., "Dual Enzyme Electrochemical Coding for Detecting DNA Hybridization" Analyst 2002, 1279-1282, The Royal Society of Chemistry.

Wang, Joseph "Survey and Summary from DNA Biosensors . . . " Nucleic Acids Research 2000, pp. 3011-3016, vol. 28, No. 16 Oxford University Press.

Wilgenbus and Lichter, "DNA Chip Technology Ante Portas" J. Mol. Med., Nov. 1999, pp. 761-768, vol. 77.

Xie et al., Amperometric Detection of Nucleic Acid at Femtomolar Levels with a Nucleic Acid/Electrochemical Activator Bilayer on Gold Electrodes, 2004, vol. 76, pp. 1611-1617.

* cited by examiner

A sulfonyl amidite

Compound A - An amino amidite

Compound B - A succinate moiety as pyridinium salt

MICROARRAY HAVING A BASE CLEAVABLE LINKER

CROSS-REFERENCE TO RELATED APPLICATIONS

This patent application is a continuation of U.S. patent application Ser. No. 11/229,757, filed Sep. 19, 2005 now abandoned and a continuation of U.S. patent application Ser. No. 11/361,160, filed Feb. 24, 2006, now U.S. Pat. No. 7,541,314, both of which applications are hereby incorporated by reference in their entirety for all purposes.

TECHNICAL FIELD

Disclosed herein are microarrays having base cleavable linker moieties attached at known locations on the microarray. Further disclosed is a process to make the microarrays having the base cleavable linkers attached at known locations. Further disclosed are oligomers synthesized in situ onto the base cleavable linkers. Further disclosed is cleaving the oligomers from the microarray to provide a pool of oligomers.

BACKGROUND

Microarray preparation methods for synthetic oligomers, including oligonucleotides (oligos) include the following: (i) spotting a solution on a prepared flat or substantially planar surface using spotting robots; (ii) in situ synthesis by printing reagents via ink jet or other computer printing technology and using standard phosphoramidite chemistry; (iii) in situ parallel synthesis using electrochemically generated acid for removal of protecting groups and using standard phosphoramidite chemistry; (iv) in situ synthesis using maskless photo-generated acid for removal of protecting groups and using regular phosphoramidite chemistry; (v) mask-directed in situ parallel synthesis using photo-cleavage of photolabile protecting groups (PLPG) and standard phosphoramidite chemistry; (vi) maskless in situ parallel synthesis using PLPG and digital photolithography and standard phosphoramidite chemistry; and (vii) electric field attraction/repulsion for depositing fully formed oligos onto known locations.

Photolithographic techniques for in situ oligo synthesis are disclosed in Fodor et al. U.S. Pat. No. 5,445,934 and the additional patents claiming priority thereto, all of which are incorporated by reference herein. Electric field attraction/repulsion microarrays are disclosed in Hollis et al. U.S. Pat. No. 5,653,939 and Heller et al. U.S. Pat. No. 5,929,208, both of which are incorporated by reference herein. An electrode microarray for in situ oligo synthesis using electrochemical deblocking is disclosed in Montgomery U.S. Pat. Nos. 6,093,302; 6,280,595, and 6,444,111 (Montgomery I, II, and III respectively), all of which are incorporated by reference herein. Another and materially different electrode array (not a microarray) for in situ oligo synthesis on surfaces separate and apart from electrodes using electrochemical deblocking is disclosed in Southern U.S. Pat. No. 5,667,667, which is incorporated by reference herein. A review of oligo microarray synthesis is provided by: Gao et al., *Biopolymers* 2004, 73:579.

U.S. patent application Ser. No. 10/243,367, filed 12 Sep. 2002 (Oleinikov) discloses a process for assembling a polynucleotide from a plurality of oligonucleotides. The claimed process provides a plurality of oligonucleotide sequences that are synthesized in situ or spotted on a microarray device. The plurality of oligonucleotide sequences is attached to a solid or porous surface of the microarray device. The oligonucleotide sequences are cleaved at a cleavable linker site to form a soluble mixture of oligonucleotides. The cleavable linker is a chemical composition having a succinate moiety bound to a nucleotide moiety such that cleavage produces a 3'-hydroxy nucleotide.

The succinate moiety disclosed in Oleinikov as a cleavable linker is bound to the solid or porous surface through an ester linkage by reacting the succinate moieties with the solid or porous surface. In general, formation of an ester linkage to an organic hydroxyl on a solid surface using a succinate is relatively difficult and often results in relatively low yield. Additionally, the reaction conditions require a relatively long period of time at relatively high temperature. Increasing yield would increase oligonucleotide density and provide more efficient production of oligonucleotides on a microarray. Oligonucleotides cleaved from the microarray disclosed in Oleinikov have a three prime hydroxyl, which may limit the use of such oligonucleotides or result in the need for an additional step to modify the three-prime hydroxyl. Disclosed herein are embodiments that provide oligonucleotides having three-prime functionality that is different from a three prime hydroxyl of Oleinikov, of which different functionality expands the use of such oligonucleotides. Further disclosed herein are embodiments that address the problems in Oleinikov of low yield and hence low oligonucleotide density at a location on a microarray by providing alternative cleavable linker chemistry, which is more reactive to hydroxyl groups on a microarray. Further disclosed herein are embodiments that address the limitations of Oleinikov with respect to attachment of oligonucleotides having a three-prime hydroxyl to a solid or porous surface by providing different three-prime chemistry.

SUMMARY

Disclosed herein is a process for forming a microarray having base cleavable sulfonyl linkers. The process comprises providing an array having known locations having a plurality of hydroxyl groups. The array comprises a surface or a matrix proximate to the surface, wherein the density of the known locations is greater than approximately 100 per square centimeter. The process further comprises bonding one or a plurality of sulfonyl amidite containing reagents to the hydroxyl groups at the known locations to form a plurality of cleavable linkers bonded to the known locations. The cleavable linkers comprise a hydroxyl moiety and a base-labile cleaving moiety. A phosphorous-oxygen bond is formed between phosphorous of the sulfonyl amidite containing reagent and oxygen of the hydroxyl groups.

Further disclosed herein is a process for forming a microarray having base cleavable sulfonyl linkers. The process comprises providing an array device having a plurality of known locations, each having a plurality of hydroxyl groups. The density of the known locations is greater than approximately 100 per square centimeter. The process further comprises bonding a plurality of sulfonyl amidite moieties to the hydroxyl groups to form a plurality of cleavable linkers attached to the array device at each known location. The cleavable linkers comprise a linker hydroxyl moiety and a base-labile cleaving moiety. A phosphorous-oxygen bond is formed between phosphorous of the sulfonyl amidite moieties and oxygen of the hydroxyl groups. The process further comprises synthesizing a plurality of oligomers onto the linker hydroxyl moieties.

Further disclosed herein is a process for forming a microarray having base cleavable sulfonyl linkers. The process comprises providing an array device having a plurality of known locations, each having a plurality of hydroxyl groups. The density of the plurality of known locations is greater than approximately 100 per square centimeter. The process further comprises bonding a plurality of sulfonyl amidite moieties to the hydroxyl groups to form a plurality of cleavable linkers bonded to the known locations. The cleavable linkers comprise a linker hydroxyl moiety and a base-labile cleaving moiety. A phosphorous-oxygen bond is formed between phosphorous of the sulfonyl amidite moieties and oxygen of the hydroxyl groups. The process further comprises synthesizing a plurality of oligomers covalently bound to the linker hydroxyl moiety. The process further comprises cleaving the oligomers from the known locations at the base-labile cleaving moiety using a cleaving base. The oligomers are recoverable. The oligomers comprising DNA and RNA have a 3' phosphate after cleaving from the solid surface.

Further disclosed herein is a process for forming a pool of oligomers produced by providing an array having known locations having a plurality of hydroxyl groups. The array comprises a surface or a matrix proximate to the surface. The density of the known locations is greater than approximately 100 per square centimeter. The process further comprises bonding a plurality of sulfonyl amidite moieties to the hydroxyl groups to form a plurality of cleavable linkers bonded to the known locations. The cleavable linkers comprise a linker hydroxyl moiety and a base-labile cleaving moiety. A phosphorous-oxygen bond is formed between phosphorous of the sulfonyl amidite moieties and oxygen of the hydroxyl groups. The process further comprises synthesizing a plurality of oligomers covalently bound to the linker hydroxyl moiety. The process further comprises cleaving the oligomers from the known locations at the base-labile cleaving moiety using a cleaving base. The oligomers comprise DNA and RNA and have a 3' phosphate after cleaving from the solid surface. The oligomers are oligonucleotides having a 3' phosphate. The pool comprises more than approximately 100 different oligonucleotides.

Further disclosed herein is a microarray having base cleavable sulfonyl linkers. The microarray comprises an array device having a plurality of known locations where each location has a plurality of reacted hydroxyl groups. The density of the plurality of known locations is greater than approximately 100 per square centimeter. The microarray further comprises a plurality of reacted sulfonyl amidite moieties bonded to the plurality of reacted hydroxyl groups to form a plurality of cleavable linkers attached to the plurality of known locations. The cleavable linkers have a linker hydroxyl group and a base-labile cleaving site. A phosphorous-oxygen bond is between phosphorous of the reacted sulfonyl amidite moieties and oxygen of the reacted hydroxyl groups.

Further disclosed herein is a microarray having base cleavable sulfonyl linkers. The microarray comprises an array device having a plurality of known locations where each location has a plurality of reacted hydroxyl groups. The density of the plurality of known locations is greater than approximately 100 per square centimeter. The microarray further comprises a plurality of reacted sulfonyl amidite moieties bonded to the plurality of reacted hydroxyl groups to form a plurality of cleavable linkers attached to the plurality of known locations. The cleavable linkers have a linker hydroxyl group and a base-labile cleaving site. A phosphorous-oxygen bond is between phosphorous of the reacted sulfonyl amidite moieties and oxygen of the reacted hydroxyl groups. The microarray further comprises oligomers bonded to the linker hydroxyl groups.

Further disclosed herein is a process for forming a microarray having cleavable succinate linkers. The process comprises providing a solid surface having free hydroxyl groups at known locations. The density of the known locations is greater than approximately 100 locations per square centimeter. The process further comprises bonding a linker moiety to the hydroxyl groups. The linker moiety comprises free amine group and a hydroxyl bonding group. The process further comprises bonding a succinate-containing moiety having free carboxyl groups to the free amine groups to form cleavable linkers attached to the known locations. The succinate-containing moieties comprise a sugar having both a nucleotide base group and a succinate group bonded to the sugar. The cleavable linkers have a base-labile cleaving site on the succinate group and a reactable hydroxyl group on the sugar group.

Further disclosed herein is a microarray having base cleavable succinate linkers. The microarray comprises a solid surface having known locations and reactive hydroxyl groups. The known locations have a density greater than approximately 100 per square centimeter. The microarray further comprises a plurality of reactive amino amidite moieties bonded to the reactive hydroxyl groups on the solid surface. The reactive amino moieties comprise an amine group and a hydroxyl bonding group. The hydroxyl bonding group is bonded to the reactive hydroxyl groups at the known locations. The microarray further comprises a plurality of reactive succinate moieties bonded to the amine groups. The reactive succinate moieties comprise a sugar group bonded to the succinate group and to a base group bonded. In an alternative embodiment, microarray further comprises oligomers bonded onto the reactable hydroxyl groups. In one or more embodiments, the sugar group is ribose and the base group is selected from the group consisting of adenine, guanine, cytosine, and uracyl, or the sugar group is deoxyribose and the base group is selected from the group consisting of adenine, guanine, cytosine, and thymine.

Further disclosed herein is a process of forming a microarray having base cleavable phosphoramidite linkers. The process comprises providing a microarray having a surface with a plurality of known locations on the surface. Each location has a plurality of hydroxyl groups, and the density of the known locations is greater than approximately 100 per square centimeter on the surface. The process further comprises bonding a plurality of base cleavable phosphoramidite linkers to the plurality of hydroxyl groups directly or by using an intermediate chemical moiety attached to the hydroxyl groups to form a plurality of cleavable linkers at the plurality of known locations. The cleavable linkers each have a linker hydroxyl group and a base-labile cleaving site. The linker hydroxyl group is protected by a protecting group, and the base-labile cleaving site is an ether linkage. Optionally, the process further comprises synthesizing oligomers onto the linker hydroxyl groups to provide a microarray of oligomers. The protecting group is removed from the linker hydroxyl groups before synthesizing the oligomers, and the oligomers at the known locations, as between different known locations, are different or the same. Optionally, the process further comprises cleaving at the base-labile cleaving site the oligomers from the surface using a cleaving base to provide a pool of cleaved oligomers.

Further disclosed herein is a pool of oligomers produced according to one or more of the processes disclosed herein, wherein the oligomers are oligonucleotides having a 3' phosphate, wherein the pool comprises more than approximately 100 different oligonucleotides. Further disclosed herein is a pool of oligomers produced according to one or more of the processes disclosed herein, wherein the oligomers are oligonucleotides having a 3' hydroxyl, wherein the pool comprises more than approximately 100 different oligonucleotides.

Further disclosed herein is a microarray having base cleavable linkers. The microarray comprises a microarray having a surface with a plurality of known locations on the surface, wherein each location has a plurality of hydroxyl groups, wherein the density of the known locations is greater than approximately 100 per square centimeter on the surface. The microarray further comprises a plurality of base cleavable linkers bonded to the plurality of hydroxyl groups to form a plurality of cleavable linkers at the plurality of known locations, wherein the cleavable linkers each have a linker hydroxyl group and a base-labile cleaving site.

DETAILED DESCRIPTION

Figure 1A:
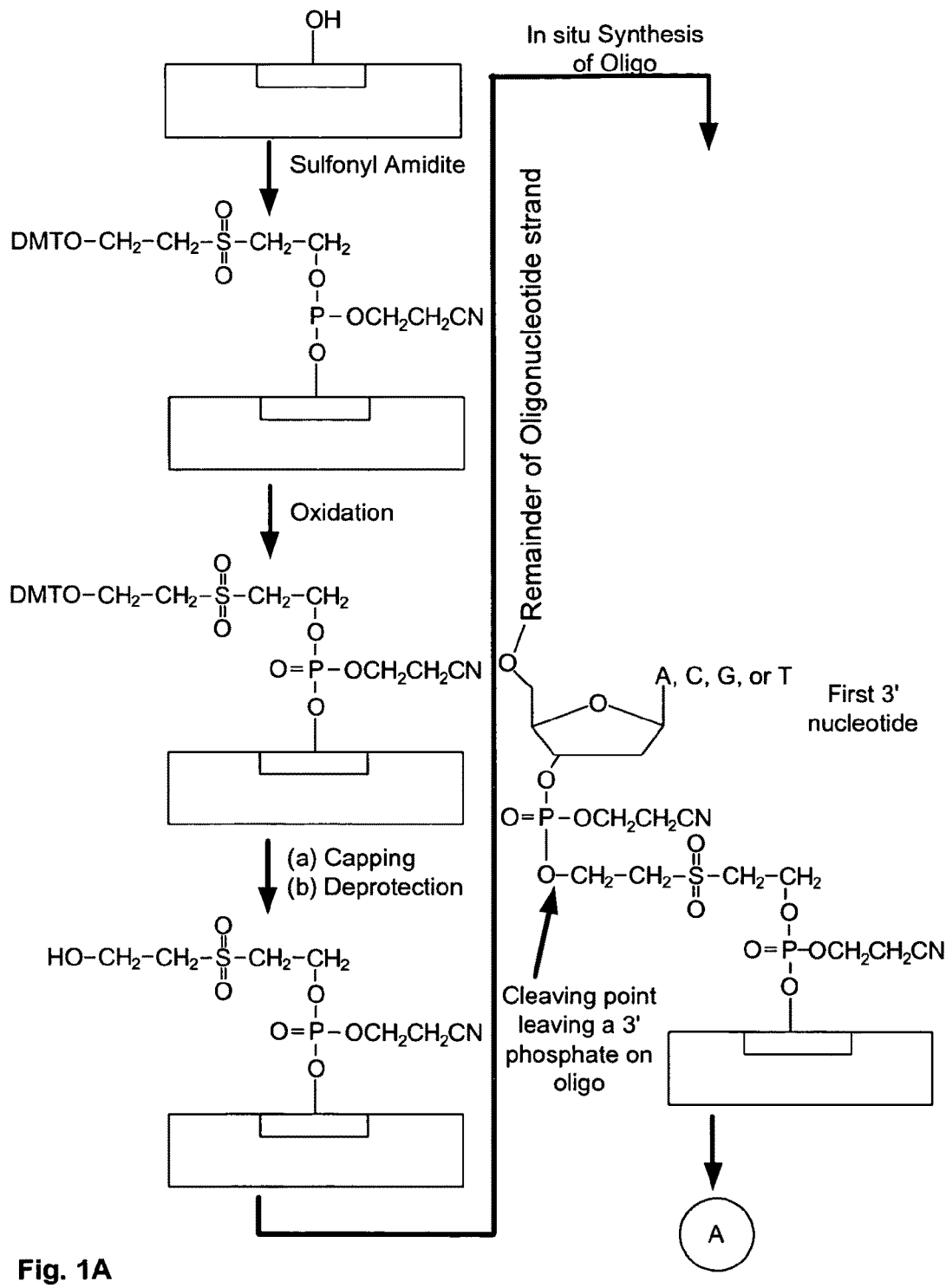
FIGS. 1A and 1B are a schematic of a cross section of a microarray device showing one known location undergoing a sequence of steps for the bonding of a cleavable linker, an oligonucleotide to the linker, and then removal of the oligonucleotide by cleaving the linker using a base.

Generally, nomenclature for chemical groups as used herein follows the recommendations of "The International Union for Pure and Applied Chemistry", Principles of Chemical Nomenclature: a Guide to IUPAC Recommendations, Leigh, G. J.; Favre, H. A. and Metanomski, W. V., Blackwell Science, 1998, the disclosure of which is incorporated by reference herein. Formation of substituted structures is limited by atom valence requirements.

"Oligomer" means a molecule of intermediate relative molecular mass, the structure of which essentially comprises a small plurality of units derived, actually or conceptually, from molecules of lower relative molecular mass. A molecule is regarded as having an intermediate relative molecular mass if it has properties which do vary significantly with the removal of one or a few of the units. If a part or the whole of the molecule has an intermediate relative molecular mass and essentially comprises a small plurality of units derived, actually or conceptually, from molecules of lower relative molecular mass, it may be described as oligomeric, or by oligomer used adjectivally. Oligomers are typically comprised of a monomer.

The term "co-oligomer" means an oligomer derived from more than one species of monomer. The term oligomer includes co-oligomers. A single stranded DNA molecule consisting of any combination of deoxyadenylate (A), deoxyguanylate (G), deoxycytidylate (C), and deoxythymidylate (T) units is an oligomer.

The term "monomer" means a molecule that can undergo polymerization thereby contributing constitutional units to the essential structure of a macromolecule such as an oligomer, co-oligomer, polymer, or co-polymer. Examples of monomers for oligonucleotides include A, C, G, T, adenylate, guanylate, cytidylate, and uridylate. Monomers for other oligomers, including polypeptides, include amino acids, vinyl chloride, and other vinyls.

The term "polymer" means a substance composed of macromolecules, which is a molecule of high relative molecular mass, the structure of which essentially comprises the multiple repetition of units derived, actually or conceptually, from molecules of low relative molecular mass. In many cases, especially for synthetic polymers, a molecule can be regarded as having a high relative molecular mass if the addition or removal of one or a few of the units has a negligible effect on the molecular properties. This statement fails in the case of certain macromolecules for which the properties may be critically dependent on fine details of the molecular structure. If a part or the whole of the molecule has a high relative molecular mass and essentially comprises the multiple repetition of units derived, actually or conceptually, from molecules of low relative molecular mass, it may be described as either macromolecular or polymeric, or by polymer used adjectivally.

The term "copolymer" means a polymer derived from more than one species of monomer. Copolymers that are obtained by copolymerization of two monomer species are sometimes termed biopolymers, those obtained from three monomers terpolymers, those obtained from four monomers quaterpolymers, etc. The term polymer includes co-polymers.

The term "polyethylene glycol" (PEG) means an organic chemical having a chain consisting of the common repeating ethylene glycol unit [—$CH_2$—$CH_2$—O—]$_n$. PEG's are typically long chain organic polymers that are flexible, hydrophilic, enzymatically stable, and biologically inert, but they do not have an ionic charge in water. In general, PEG can be divided into two categories. First, there is polymeric PEG having a molecular weight ranging from 1000 to greater than 20,000. Second, there are PEG-like chains having a molecular weight that is less than 1000. Polymeric PEG has been used in bioconjugates, and numerous reviews have described the attachment of this linker moiety to various molecules. PEG has been used as a linker, where the short PEG-like linkers can be classified into two types, the homo-

[X—(CH$_2$—CH$_2$—O)$_n$]—X and heterobifunctional [X—(CH$_2$—CH$_2$—O)$_n$]—Y spacers.

The term "PEG derivative" means an ethylene glycol derivative having the common repeating unit of PEG. Examples of PEG derivatives include, but are not limited to, diethylene glycol (DEG), tetraethylene glycol (TEG), polyethylene glycol having primary amino groups, di(ethylene glycol) mono allyl ether, di(ethylene glycol) mono tosylate, tri(ethylene glycol) mono allyl ether, tri(ethylene glycol) mono tosylate, tri(ethylene glycol) mono benzyl ether, tri(ethylene glycol) mono trityl ether, tri(ethylene glycol) mono chloro mono methyl ether, tri(ethylene glycol) mono tosyl mono allyl ether, tri(ethylene glycol) mono allyl mono methyl ether, tetra(ethlyne glycol) mono allyl ether, tetra(ethylene glycol) mono methyl ether, tetra(ethylene glycol) mono tosyl mono allyl ether, tetra(ethylene glycol) mono tosylate, tetra(ethylene glycol) mono benzyl ether, tetra(ethylene glycol) mono trityl ether, tetra(ethylene glycol) mono 1-hexenyl ether, tetra(ethylene glycol) mono 1-heptenyl ether, tetra(ethylene glycol) mono 1-octenyl ether, tetra(ethylene glycol) mono 1-decenyl ether, tetra(ethylene glycol) mono 1-undecenyl ether, penta(ethylene glycol) mono methyl ether, penta(ethylene glycol) mono allyl mono methyl ether, penta(ethylene glycol) mono tosyl mono methyl ether, penta(ethylene glycol) mono tosyl mono allyl ether, hexa(ethylene glycol) mono allyl ether, hexa(ethylene glycol) mono methyl ether, hexa(ethylene glycol) mono benzyl ether, hexa(ethylene glycol) mono trityl ether, hexa(ethylene glycol) mono 1-hexenyl ether, hexa(ethylene glycol) mono 1-heptenyl ether, hexa(ethylene glycol) mono 1-octenyl ether, hexa(ethylene glycol) mono 1-decenyl ether, hexa(ethylene glycol) mono 1-undecenyl ether, hexa(ethylene glycol) mono 4-benzophenonyl mono 1-undecenyl ether, hepta(ethylene glycol) mono allyl ether, hepta(ethylene glycol) mono methyl ether, hepta(ethylene glycol) mono tosyl mono methyl ether, hepta(ethylene glycol) monoallyl mono methyl ether, octa(ethylene glycol) mono allyl ether, octa(ethylene glycol) mono tosylate, octa(ethylene glycol) mono tosyl mono allyl ether, undeca(ethylene glycol) mono methyl ether, undeca(ethylene glycol) mono allyl mono methyl ether, undeca(ethylene glycol) mono tosyl mono methyl ether, undeca(ethylene glycol) mono allyl ether, octadeca(ethylene glycol) mono allyl ether, octa(ethylene glycol), deca(ethylene glycol), dodeca(ethylene glycol), tetradeca(ethylene glycol), hexadeca(ethylene glycol), octadeca(ethylene glycol), benzophenone-4-hexa(ethylene glycol) allyl ether, benzophenone-4-hexa(ethylene glycol) hexenyl ether, benzophenone-4-hexa(ethylene glycol) octenyl ether, benzophenone-4-hexa(ethylene glycol) decenyl ether, benzophenone-4-hexa(ethylene glycol) undecenyl ether, 4-fluorobenzophenone-4'-hexa(ethylene glycol) allyl ether, 4-fluorobenzophenone-4'-hexa(ethylene glycol) undecenyl ether, 4-hydroxybenzophenone-4'-hexa(ethylene glycol) allyl ether, 4-hydroxybenzophenone-4'-hexa(ethylene glycol) undecenyl ether, 4-hydroxybenzophenone-4'-tetra(ethylene glycol) allyl ether, 4-hydroxybenzophenone-4'-tetra(ethylene glycol) undecenyl ether, 4-morpholinobenzophenone-4'-hexa(ethylene glycol) allyl ether, 4-morpholinobenzophenone-4'-hexa(ethylene glycol) undecenyl ether, 4-morpholinobenzophenone-4'-tetra(ethylene glycol) allyl ether, and 4-morpholinobenzophenone-4'-tetra(ethylene glycol) undecenyl ether.

The term "polyethylene glycol having primary amino groups" refers to polyethylene glycol having substituted primary amino groups in place of the hydroxyl groups. Substitution can be up to 98% in commercial products ranging in molecular weight from 5,000 to 20,000 Da.

The term "alkyl" means a straight or branched chain alkyl group containing up to approximately 20 but preferably up to 8 carbon atoms. Examples of alkyl groups include but are not limited to the following: methyl, ethyl, n-propyl, iso-propyl, n-butyl, isobutyl, sec-butyl, tert-butyl, n-pentyl, iso-pentyl, neopentyl, tert-pentyl, isohexyl, n-hexyl, n-heptyl, and n-octyl. A substituted alkyl has one or more hydrogen atoms substituted by other groups or a carbon replaced by a divalent, trivalent, or tetravalent group or atom. Although alkyls by definition have a single radical, as used herein, alkyl includes groups that have more than one radical to meet valence requirements for substitution.

The term "alkenyl" means a straight or branched chain alkyl group having at least one carbon-carbon double bond, and containing up to approximately 20 but preferably up to 8 carbon atoms. Examples of alkenyl groups include, but are not limited to, vinyl, 1-propenyl, 2-butenyl, 1,3-butadienyl, 2-pentenyl, 2,4-hexadienyl, 4-(ethyl)-1,3-hexadienyl, and 2-(methyl)-3-(propyl)-1,3-butadienyl. A substituted alkenyl has one or more hydrogen atoms substituted by other groups or a carbon replaced by a divalent, trivalent, or tetravalent group or atom. Although alkenyls by definition have a single radical, as used herein, alkenyl includes groups that have more than one radical to meet valence requirements for substitution.

The term "alkynyl" means a straight or branched chain alkyl group having a single radical, having at least one carbon-carbon triple bond, and containing up to approximately 20 but preferably up to 8 carbon atoms. Examples of alkynyl groups include, but are not limited to, the ethynyl, 1-propynyl, 2-propynyl, 1-butynyl, 2-butynyl, 3-butynyl, 4-pentynyl, 5-hexynyl, 6-heptynyl, 7-octynyl, 1-methyl-2-butynyl, 2-methyl-3-pentynyl, 4-ethyl-2-pentynyl, and 5,5-methyl-1,3-hexynyl. A substituted alkynyl has one or more hydrogen atoms substituted by other groups or a carbon replaced by a divalent, trivalent, or tetravalent group or atom. Although alkynyls by definition have a single radical, as used herein, alkynyl includes groups that have more than one radical to meet valence requirements for substitution.

The term "cycloalkyl" means an alkyl group forming at least one ring, wherein the ring has approximately 3 to 14 carbon atoms. Examples of cycloalkyl groups include but are not limited to the following: cyclopropyl, cyclobutyl, cyclopentyl, and cyclohexyl. A substituted cycloalkyl has one or more hydrogen atoms substituted by other groups or a carbon replaced by a divalent, trivalent, or tetravalent group or atom. Although cycloalkyls by definition have a single radical, as used herein, cycloalkyl includes groups that have more than one radical to meet valence requirements for substitution.

The term "cycloalkenyl" means an alkenyl group forming at least one ring and having at least one carbon-carbon double bond within the ring, wherein the ring has approximately 3 to 14 carbon atoms. Examples of cycloalkenyl groups include, but are not limited to, cyclopropenyl, cyclobutenyl, cyclopentenyl, 1,3-cyclopentadienyl, and cyclohexenyl. A substituted cycloalkenyl has one or more hydrogens substituted by other groups or a carbon replaced by a divalent, trivalent, or tetravalent group or atom. Although cycloalkenyls by definition have a single radical, as used herein, cycloalkenyl includes groups that have more than one radical to meet valence requirements for substitution.

The term "cycloalkynyl" means an alkynyl group forming at least one ring and having at least one carbon-carbon triple bond, wherein the ring contains up to approximately 14 carbon atoms. A group forming a ring having at least one triple bond and having at least one double bond is a cycloalkynyl group. An example of a cycloalkynyl group includes, but is not limited to, cyclooctyne. A substituted cycloalkynyl has one or more hydrogen atoms substituted by other groups. Although cycloalkynyls by definition have a single radical, as used herein, cycloalkynyl includes groups that have more than one radical to meet valence requirements for substitution.

The term "aryl" means an aromatic carbon ring group having a single radical and having approximately 4 to 20 carbon atoms. Examples of aryl groups include, but are not limited to, phenyl, naphthyl, and anthryl. A substituted aryl has one or more hydrogen atoms substituted by other groups. Although aryls by definition have a single radical, as used herein, aryl includes groups that have more than one radical to meet valence requirements for substitution. An aryl group can be a part of a fused ring structure such as N-hydroxysuccinimide bonded to phenyl (benzene) to form N-hydroxyphthalimide.

The term "hetero" when used in the context of chemical groups, or "heteroatom" means an atom other than carbon or hydrogen. Preferred examples of heteroatoms include oxygen, nitrogen, phosphorous, sulfur, boron, silicon, and selenium.

The term "heterocyclic ring" means a ring structure having at least one ring moiety having at least one heteroatom forming a part of the ring, wherein the heterocyclic ring has approximately 4 to 20 atoms connected to form the ring structure. An example of a heterocyclic ring having 6 atoms is pyridine with a single hereroatom. Additional examples of heterocyclic ring structures having a single radical include, but are not limited to, acridine, carbazole, chromene, imidazole, furan, indole, quinoline, and phosphinoline. Examples of heterocyclic ring structures include, but are not limited to, aziridine, 1,3-dithiolane, 1,3-diazetidine, and 1,4,2-oxazaphospholidine. Examples of heterocyclic ring structures having a single radical include, but are not limited to, fused aromatic and non-aromatic structures: 2H-furo[3,2-b]pyran, 5H-pyrido[2,3-d]-o-oxazine, 1H-pyrazolo[4,3-d]oxazole, 4H-imidazo[4,5-d]thiazole, selenazolo[5,4-j]benzothiazole, and cyclopenta[b]pyran. Heterocyclic rings can have one or more radicals to meet valence requirements for substitution.

The term "polycyclic" or "polycyclic group" means a carbon ring structure having more than one ring, wherein the polycyclic group has approximately 4 to 20 carbons forming the ring structure and has a single radical. Examples of polycyclic groups include, but are not limited to, bicyclo[1.1.0]butane, bicyclo[5.2.0]nonane, and tricycle[5.3.1.1]dodecane. Polycyclic groups can have one or more radicals to meet valence requirements for substitution.

The term "halo" or "halogen" means fluorine, chlorine, bromine, or iodine.

The term "heteroatom group" means one heteroatom or more than one heteroatoms bound together and having two free valences for forming a covalent bridge between two atoms. For example, the oxy radical, —O— can form a bridge between two methyls to form $CH_3$—O—$CH_3$ (dimethyl ether) or can form a bridge between two carbons to form an epoxy such as cis or trans 2,3-epoxybutane,

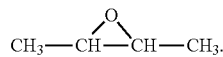

As used herein and in contrast to the normal usage, the term heteroatom group will be used to mean the replacement of groups in an alkyl, alkenyl, alkynyl, cycloalkyl, cycloalkenyl, and cycloalkynyl and not the formation of cyclic bridges, such as an epoxy, unless the term cyclic bridge is used with the term heteroatom group to denote the normal usage.

Examples of heteroatom groups, using the nomenclature for hetero bridges (such as an epoxy bridge), include but are not limited to the following: azimino (—N=N—HN—), azo (—N=N—), biimino (—NH—NH—), epidioxy (—O—O—), epidithio (—S—S—), epithio (—S—), epithioximino (—S—O—NH—), epoxy (—O—), epoxyimino (—O—NH—), epoxynitrilo (—O—N=), epoxythio (—O—S—), epoxythioxy(—O—S—O—), furano (—$CH_2$O—), imino (—NH—), and nitrilo (—N=). Examples of heteroatom groups using the nomenclature for forming acyclic bridges include but are not limited to the following: epoxy (—O—), epithio (—S—), episeleno (—Se—), epidioxy (—O—O—), epidithio (—S—S—), lambda$^4$-sulfano (—$SH_2$—), epoxythio (—O—S—), epoxythioxy (—O—S—O—), epoxyimino (—O—NH—), epimino (—NH—), diazano (—NH—NH—), diazeno (—N=N—), triaz[1]eno (—N=N—NH—), phosphano (—PH—), stannano (—$SnH_2$—), epoxymethano (—O—$CH_2$—), epoxyethano (—O—$CH_2$—$CH_2$—), epoxyprop[1]eno

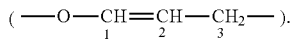

The term "bridge" means a connection between one part of a ring structure to another part of the ring structure by a hydrocarbon bridge. Examples of bridges include but are not limited to the following: methano, ethano, etheno, propano, butano, 2-buteno, and benzeno.

The term "hetero bridge" means a connection between one part of a ring structure to another part of the ring structure by one or more heteroatom groups, or a ring formed by a heterobridge connecting one part of a linear structure to another part of the linear structure, thus forming a ring.

The term "oxy" means the divalent radical —O—.
The term "oxo" means the divalent radical =O.
The term "carbonyl" means the group

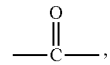

wherein the carbon has two radicals for bonding.
The term "amide" or "acylamino" means the group

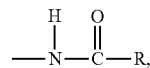

wherein the nitrogen has one single radical for bonding and R is hydrogen or an unsubstituted or substituted alkyl, alkenyl, alkynyl, cycloalkyl, cycloalkenyl, cycloalkynyl, aryl, heterocyclic ring, or polycyclic group.

The term "alkoxy" means the group —O—R, wherein the oxygen has a single radical and R is hydrogen or an unsubstituted or substituted alkyl, alkenyl, alkynyl, cycloalkyl, cycloalkenyl, cycloalkynyl, aryl, heterocyclic ring, or polycyclic group. Examples of alkoxy groups where the R is an alkyl include but are not limited to the following: methoxy, ethoxy, propoxy, butoxy, pentoxy, hexoxy, heptoxy, octoxy, 1,1-dimethylethoxy, 1,1-dimethylpropoxy, 1,1-dimethylbutoxy, 1,1-dimethylpentoxy, 1-ethyl-1-methylbutoxy, 2,2-dimethylpropoxy, 2,2-dimethylbutoxy, 1-methyl-1-ethylpropoxy, 1,1-diethylpropoxy, 1,1,2-trimethylpropoxy, 1,1,2-trimethylbutoxy, 1,1,2,2-tetramethylpropoxy. Examples of alkoxy groups where the R is an alkenyl group include but are not limited to the following: ethenyloxy, 1-propenyloxy, 2-propenyloxy, 1-butenyloxy, 2-butenyloxy, 3-butenyloxy, 1-methyl-prop-2-enyloxy, 1,1-dimethyl-prop-2-enyloxy, 1,1,2-trimethyl-prop-2-enyloxy, and 1,1-dimethyl-but-2-enyloxy, 2-ethyl-1,3-dimethyl-but-1-enyloxy. Examples of alkyloxy groups where the R is an alkynyl include but are not limited to the following: ethynyloxy, 1-propynyloxy, 2-propynyloxy, 1-butynyloxy, 2-butynyloxy, 3-butynyloxy, 1-methyl-prop-2-ynyloxy, 1,1-dimethyl-prop-2-ynyloxy, and 1,1-dimethyl-but-2-ynyloxy, 3-ethyl-3-methyl-but-1-ynyloxy. Examples of alkoxy groups where the R is an aryl group include but are not limited to the following: phenoxy, 2-naphthyloxy, and 1-anthyloxy.

The term "acyl" means the group

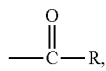

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group. Examples of acyl groups include but are not limited to the following: acetyl, propionyl, butyryl, isobutyryl, valeryl, isovaleryl, acryloyl, propioloyl, mathacryloyl, crotonoyl, isocrotonoyl, benzoyl, and naphthoyl.

The term "acyloxy" means the group

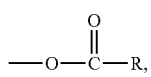

wherein the oxygen has a single radical and R is hydrogen or an unsubstituted or substituted alkyl, alkenyl, alkynyl, cycloalkyl, cycloalkenyl, cycloalkynyl, aryl, heterocyclic ring, or polycyclic group. Examples of acyloxy groups include but are not limited to the following: acetoxy, ethylcarbonyloxy, 2-propenylcarbonyloxy, pentylcarbonyloxy, 1-hexynylcarbonyloxy, benzoyloxy, cyclohexylcarbonyloxy, 2-naphthoyloxy, 3-cyclodecenylcarbonyloxy.

The term "oxycarbonyl" means the group

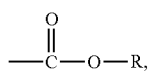

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group. Examples of oxycarbonyl groups include but are not limited to the following: methoxycarbonyl, ethoxycarbonyl, isopropyloxycarbonyl, phenoxycarbonyl, and cyclohexyloxycarbonyl.

The term "acyloxycarbonyl" means the group

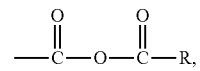

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "alkoxycarbonyloxy" means the group

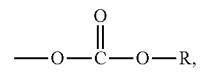

wherein the oxygen has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "carboxy" means the group —C(O)OH, wherein the carbon has a single radical.

The term "imino" or "nitrene" means the group =N—R, wherein the nitrogen has two radicals and R is hydrogen or an unsubstituted or substituted alkyl, alkenyl, alkynyl, cycloalkyl, cycloalkenyl, cycloalkynyl, aryl, heterocyclic ring, or polycyclic group.

The term "amino" means the group —NH2, where the nitrogen has a single radical.

The term "secondary amino" means the group —NH—R, wherein the nitrogen has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "tertiary amino" means the group

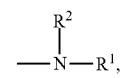

wherein the nitrogen has a single radical and R1 and R2 are independently selected from the group consisting of unsubstituted and substituted alkyl, alkenyl, alkynyl, cycloalkyl, cycloalkenyl, cycloalkynyl, aryl, heterocyclic ring, and polycyclic group.

The term "hydrazi" means the group —NH—NH—, wherein the nitrogens have single radicals bound to the same atom. The term "hydrazo" means the group —NH—NH—, wherein the nitrogens have single radicals bound to the different atoms.

The term "hydrazino" means the group NH$_2$—NH—, wherein the nitrogen has a single radical.

The term "hydrazono" means the group NH$_2$—N=, wherein the nitrogen has two radicals.

The term "hydroxyimino" means the group HO—N=, wherein the nitrogen has two radicals.

The term "alkoxyimino" means the group R—O—N=, wherein the nitrogen has two radicals and R is an unsubstituted or substituted alkyl, alkenyl, alkynyl, cycloalkyl, cycloalkenyl, cycloalkynyl, aryl, heterocyclic ring, or polycyclic group.

The term "azido" means the group N₃—, wherein the nitrogen has one radical.

The term "azoxy" means the group —N(O)=N—, wherein the nitrogens have one radical.

The term "alkazoxy" means the group R—N(O)=N—, wherein the nitrogen has one radical and R is hydrogen or an unsubstituted or substituted alkyl, alkenyl, alkynyl, cycloalkyl, cycloalkenyl, cycloalkynyl, aryl, heterocyclic ring, or polycyclic group. Azoxybenzene is an example compound.

The term "cyano" means the group —CN. The term "isocyano" means the group —NC. The term "cyanato" means the group —OCN. The term "isocyanato" means the group —NCO. The term "fulminato" means the group —ONC. The term "thiocyanato" means the group —SCN. The term "isothiocyanato" means the group —NCS. The term "selenocyanato" means the group —SeCN. The term "isoselenocyanato" means the group —NCSe.

The term "carboxyamido" or "acylamino" means the group

wherein the nitrogen has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "acylimino" means the group

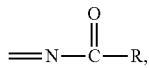

wherein the nitrogen has two radicals and R is hydrogen or an unsubstituted or substituted alkyl, alkenyl, alkynyl, cycloalkyl, cycloalkenyl, cycloalkynyl, aryl, heterocyclic ring, or polycyclic group.

The term "nitroso" means the group O=N—, wherein the nitrogen has a single radical.

The term "aminooxy" means the group —O—NH₂, wherein the oxygen has a single radical.

The term "carxoimidioy" means the group

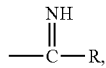

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "hydrazonoyl" means the group

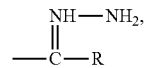

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "hydroximoyl" or "oxime" means the group

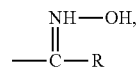

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "hydrazino" means the group

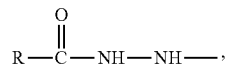

wherein the nitrogen has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "amidino" means the group

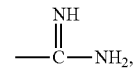

wherein the carbon has a single radical.

The term "sulfide" means the group —S—R, wherein the sulfur has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "thiol" means the group —S—, wherein the sulfur has two radicals. Hydrothiol means —SH.

The term "thioacyl" means the group —C(S)—R, wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "sulfoxide" means the group

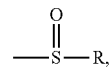

wherein the sulfur has a single radical and R is hydrogen or an unsubstituted or substituted alkyl, alkenyl, alkynyl, cycloalkyl, cycloalkenyl, cycloalkynyl, aryl, heterocyclic ring, or polycyclic group. The term "thiosulfoxide" means the substitution of sulfur for oxygen in sulfoxide; the term includes substitution for an oxygen bound between the sulfur and the R group when the first carbon of the R group has been substituted by an oxy group and when the sulfoxide is bound to a sulfur atom on another group.

The term "sulfone" means the group

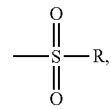

wherein the sulfur has a single radical and R is hydrogen or an unsubstituted or substituted alkyl, alkenyl, alkynyl, cycloalkyl, cycloalkenyl, cycloalkynyl, aryl, heterocyclic ring, or polycyclic group. The term "thiosulfone" means substitution of sulfur for oxygen in one or two locations in sulfone; the term includes substitution for an oxygen bound between the sulfur and the R group when the first carbon of the R group has been substituted by an oxy group and when the sulfone is bound to a sulfur atom on another group.

The term "sulfate" means the group

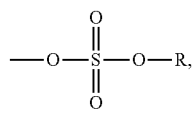

wherein the oxygen has a single radical and R is hydrogen or an unsubstituted or substituted alkyl, alkenyl, alkynyl, cycloalkyl, cycloalkenyl, cycloalkynyl, aryl, heterocyclic ring, or polycyclic group. The term "thiosulfate" means substitution of sulfur for oxygen in one, two, three, or four locations in sulfate.

The term "phosphoric acid ester" means the group $R^1R^2PO_4$—, wherein the oxygen has a single radical and $R^1$ is selected from the group consisting of hydrogen and unsubstituted and substituted alkyl, alkenyl, alkynyl, cycloalkyl, cycloalkenyl, cycloalkynyl, aryl, heterocyclic ring, and polycyclic group, and $R^2$ is selected from the group consisting of unsubstituted and substituted alkyl, alkenyl, alkynyl, cycloalkyl, cycloalkenyl, cycloalkynyl, aryl, heterocyclic ring, and polycyclic group.

The term "substituted" or "substitution," in the context of chemical species, means independently selected from the group consisting of (1) the replacement of a hydrogen on at least one carbon by a monovalent radical, (2) the replacement of two hydrogens on at least one carbon by a divalent radical, (3) the replacement of three hydrogens on at least one terminal carbon (methyl group) by a trivalent radical, (4) the replacement of at least one carbon and the associated hydrogens (e.g., methylene group) by a divalent, trivalent, or tetravalent radical, and (5) combinations thereof. Meeting valence requirements restricts substitution. Substitution occurs on alkyl, alkenyl, alkynyl, cycloalkyl, cycloalkenyl, cycloalkynyl, aryl, heterocyclic ring, and polycyclic groups, providing substituted alkyl, substituted alkenyl, substituted alkynyl, substituted cycloalkyl, substituted cycloalkenyl, substituted cycloalkynyl, substituted aryl group, substituted heterocyclic ring, and substituted polycyclic groups.

The groups that are substituted on an alkyl, alkenyl, alkynyl, cycloalkyl, cycloalkenyl, cycloalkynyl, aryl, heterocyclic ring, and polycyclic groups are independently selected from the group consisting of alkyl, alkenyl, alkynyl, cycloalkyl, cycloalkenyl, cycloalkynyl, aryl, heterocyclic ring, polycyclic group, halo, heteroatom group, oxy, oxo, carbonyl, amide, alkoxy, acyl, acyloxy, oxycarbonyl, acyloxycarbonyl, alkoxycarbonyloxy, carboxy, imino, amino, secondary amino, tertiary amino, hydrazi, hydrazino, hydrazono, hydroxyimino, azido, azoxy, alkazoxy, cyano, isocyano, cyanato, isocyanato, thiocyanato, fulminato, isothiocyanato, isoselenocyanato, selenocyanato, carboxyamido, acylimino, nitroso, aminooxy, carboximidoyl, hydrazonoyl, oxime, acylhydrazino, amidino, sulfide, thiol, sulfoxide, thiosulfoxide, sulfone, thiosulfone, sulfate, thiosulfate, hydroxyl, formyl, hydroxyperoxy, hydroperoxy, peroxy acid, carbamoyl, trimethyl silyl, nitrilo, nitro, aci-nitro, nitroso, semicarbazono, oxamoyl, pentazolyl, seleno, thiooxi, sulfamoyl, sulfenamoyl, sulfeno, sulfinamoyl, sulfino, sulfinyl, sulfo, sulfoamino, sulfonato, sulfonyl, sulfonyldioxy, hydrothiol, tetrazolyl, thiocarbamoyl, thiocarbazono, thiocarbodiazono, thiocarbonohydrazido, thiocarbonyl, thiocarboxy, thiocyanato, thioformyl, thioacyl, thiosemicarbazido, thiosulfino, thiosulfo, thioureido, thioxo, triazano, triazeno, triazinyl, trithio, trithiosulfo, sulfinimidic acid, sulfonimidic acid, sulfinohydrazonic acid, sulfonohydrazonic acid, sulfinohydroximic acid, sulfonohydroximic acid, and phosphoric acid ester, and combinations thereof.

As an example of a substitution, replacement of one hydrogen atom on ethane by a hydroxyl provides ethanol, and replacement of two hydrogens by an oxo on the middle carbon of propane provides acetone (dimethyl ketone.) As a further example, replacement the middle carbon (the methenyl group) of propane by the oxy radical (—O—) provides dimethyl ether ($CH_3$—O—$OCH_3$.) As a further example, replacement of one hydrogen atom on benzene by a phenyl group provides biphenyl.

As provided above, heteroatom groups can be substituted inside an alkyl, alkenyl, or alkylnyl group for a methylene group (:$CH_2$) thus forming a linear or branched substituted structure rather than a ring or can be substituted for a methylene inside of a cycloalkyl, cycloalkenyl, or cycloalkynyl ring thus forming a heterocyclic ring. As a further example, nitrilo (—N=) can be substituted on benzene for one of the carbons and associated hydrogen to provide pyridine, or and oxy radical can be substituted to provide pyran.

The term "unsubstituted" means that no hydrogen or carbon has been replaced on an alkyl, alkenyl, alkynyl, cycloalkyl, cycloalkenyl, cycloalkynyl, or aryl group.

The term "linker" means a molecule having one end attached or capable of attaching to a solid surface and the other end having a reactive group that is attached or capable of attaching to a chemical species of interest such as a small molecule, an oligomer, or a polymer. A linker may already be bound to a solid surface and/or may already have a chemical species of interest bound to its reactive group. A linker may have a protective group attached to its reactive group, where the protective group is chemically or electrochemically removable. A linker may comprise more than one molecule, where the molecules are covalently joined in situ to form the linker having the desired reactive group projecting away from a solid surface.

The term "spacer" or "linker moiety" means a molecule having one end attached or capable of attaching to the reactive group of a linker or porous reaction layer and the other end having a reactive group that is attached or capable of attaching to a chemical species of interest such as a small molecule, an oligomer, or a polymer. A spacer may already be bound to a linker or a porous reaction layer and/or may already have a chemical species of interest bound to its reactive group. A spacer may have a protective group attached to its reactive group, where the protective group is chemically or electrochemically removable. A spacer may be formed in situ on a linker or porous reaction layer. A spacer may be formed and then attached to a linker already attached to a solid surface or attached to a porous reaction layer on the solid surface. A spacer may be externally synthesized on a chemical species of interest followed by attachment to a linker already attached to a solid surface or attached to a porous reaction layer on the solid surface. A chemical species of interest may be attached to a spacer that is attached to a linker where the entire structure is then attached to a solid surface at a reactive sight on the solid surface. The purpose of a spacer is to extend the distance between a molecule of interest and a solid surface.

The term "combination linker and spacer" means a linker having both the properties of a linker and a spacer. A combination linker and spacer may be synthesized in situ or synthesized externally and attached to a solid surface.

The term "coating" means a thin layer of material that is chemically and/or physically bound to a solid surface. A coating may be attached to a solid surface by mechanical interlocking as well as by van der Waals forces (dispersion forces and dipole forces), electron donor-acceptor interactions, metallic coordination/complexation, covalent bonding, or a combination of the aforementioned. A coating can provide a reactive group for direct attachment of a chemical species of interest, attachment of a linker, or attachment of a combination linker and spacer. A coating can be polymerized and/or cross-linked in situ.

The term "reactive" or "reaction" as used in reactive or reaction coating or reactive or reaction layer means that there is a chemical species or bound group within the layer that is capable of forming a covalent bond for attachment of a linker, spacer, or other chemical species to the layer or coating.

The term "porous" as used in porous reactive layer or coating means that there are non-uniformities within the layer or coating to allow molecular species to diffuse into and through the layer or coating.

The term "adsorption" or "adsorbed" means a chemical attachment by van der Waals forces (dispersion forces and dipole forces), electron donor-acceptor interactions, or metallic coordination/complexation, or a combination of the aforementioned forces. After adsorption, a species may covalently bind to a surface, depending on the surface, the species, and the environmental conditions.

The term "microarray" refers to, in general, planer surface having specific spots that are usually arranged in a column and row format, wherein each spot can be used for some type of chemical or biochemical analysis, synthesis, or method. The spots on a microarray are typically smaller than 100 micrometers. The term "electrode microarray" refers to a microarray of electrodes, wherein the electrodes are the specific spots on the microarray.

The term "synthesis quality" refers to, in general, the average degree of similarity between a desired or designed chemical or biochemical species and the species actually synthesized. The term can refer to other issues in a synthesis such as the effect of a layer or coating on the synthesis quality achieved.

The term "salvation" means a chemical process in which solvent molecules and molecules or ions of a solute combine to form a compound, wherein the compound is generally a loosely bound complex held together by van der Waals forces (dispersion forces and dipole forces), acid-base interactions (electron donor acceptor interactions), ionic interaction, or metal complex interactions but not covalent bonds. In water, the pH of the water can affect solvation of dissociable species such as acids and bases. In addition, the concentration of salts as well as the charge on salts can affect salvation.

The term "agarose" means any commercially available agarose. Agarose is a polysaccharide biopolymer and is usually obtained from seaweed. Agarose has a relatively large number of hydroxyl groups, which provide for high water solubility. Agarose is available commercially in a wide ranger of molecular weights and properties.

The term "controlled pore glass" means any commercially available controlled pore glass material suitable for coating purposes. In general, controlled pore glass (CPG) is an inorganic glass material having a high surface area owing to a large amount of void space.

The term "monosaccharide" means one sugar molecule unlinked to any other sugars. Examples of monosaccharides include allose, altrose, arabinose, deoxyribose, erythrose, fructose (D-Levulose), galactose, glucose, gulose, idose, lyxose, mannose, psicose, ribose, ribulose, sedoheptulose, D-sorbitol, sorbose, sylulose, L-rhamnose (6-Deoxy-L-mannose), tagatose, talose, threose, xylulose, and xylose.

The term "disaccharide" means two sugars linked together to form one molecule. Examples of disaccharides include amylose, cellobiose (4-β-D-glucopyranosyl-D-glucopyranose), lactose, maltose (4-O-α-D-glucopyranosyl-D-glucose), melibiose (6-O-α-D-Galactopyranosyl-D-glucose), palatinose (6-O-α-D-Glucopyranosyl-D-fructose), sucrose, and trehalose (α-D-Glucopyranosyl-α-D-glucopyranoside).

The term "trisaccharide" means three sugars linked together to form one molecule. Examples of a trisaccharides include raffinose (6-O-α-D-Galactopyranosyl-D-glucopyranosyl-β-D-fructofuranoside) and melezitose (O-α-D-glucopyranosyl-(1→3)-β-D-fructofuranosyl-α-D-glucopyranoside).

The term "polysaccharide" means more than three sugars linked together to form one molecule, but more accurately means a sugar-based polymer or oligomer. Examples of polysaccharides include inulin, dextran, starches, and cellulose. Dextran is a polymer composed of glucose subunits (mers.)

The term "linker hydroxyl group" means a hydroxyl group on a linker moiety, wherein the hydroxyl group is initially protected by a protecting group such as MMT or DMT. After deprotection, the hydroxyl group becomes reactable. For example, after deprotection, a phosphoramidite may be bonded to the linker hydroxyl group to form a synthetic oligonucleotide.

Disclosed herein is a process for forming a microarray having base cleavable sulfonyl linkers. The process comprises providing an array having known locations having a plurality of hydroxyl groups. The array comprises a surface or a matrix proximate to the surface, wherein the density of the known locations is greater than approximately 100 per square centimeter. The process further comprises bonding one or a plurality of sulfonyl amidite containing reagents to the hydroxyl groups at the known locations to form a plurality of cleavable linkers bonded to the known locations. The cleavable linkers comprise a hydroxyl moiety and a base-labile cleaving moiety. A phosphorous-oxygen bond is formed between phosphorous of the sulfonyl amidite containing reagent and oxygen of the hydroxyl groups.

Further disclosed herein is a process for forming a microarray having base cleavable sulfonyl linkers. The process comprises providing an array device having a plurality of known locations, each having a plurality of hydroxyl groups. The density of the known locations is greater than approximately 100 per square centimeter. The process further comprises bonding a plurality of sulfonyl amidite moieties to the hydroxyl groups to form a plurality of cleavable linkers attached to the array device at each known location. The cleavable linkers comprise a linker hydroxyl moiety and a base-labile cleaving moiety. A phosphorous-oxygen bond is formed between phosphorous of the sulfonyl amidite moieties and oxygen of the hydroxyl groups. The process further comprises synthesizing a plurality of oligomers onto the linker hydroxyl moieties.

Further disclosed herein is a process for forming a microarray having base cleavable sulfonyl linkers. The process comprises providing an array device having a plurality of known locations, each having a plurality of hydroxyl groups. The density of the plurality of known locations is greater than approximately 100 per square centimeter. The process further comprises bonding a plurality of sulfonyl amidite moieties to the hydroxyl groups to form a plurality of cleavable linkers bonded to the known locations. The cleavable linkers comprise a linker hydroxyl moiety and a base-labile cleaving moiety. A phosphorous-oxygen bond is formed between phosphorous of the sulfonyl amidite moieties and oxygen of the hydroxyl groups. The process further comprises synthesizing a plurality of oligomers covalently bound to the linker hydroxyl moiety. The process further comprises cleaving the oligomers from the known locations at the base-labile cleaving moiety using a cleaving base. The oligomers are recoverable. The oligomers comprising DNA and RNA have a 3' phosphate after cleaving from the solid surface.

In one or more embodiments, the cleaving base is selected from the group consisting of ammonium hydroxide, electrochemically generated base, sodium hydroxide, potassium hydroxide, methylamine, and ethylamine and combinations thereof.

Further disclosed herein is a process for forming a pool of oligomers produced by providing an array having known locations having a plurality of hydroxyl groups. The array comprises a surface or a matrix proximate to the surface. The density of the known locations is greater than approximately 100 per square centimeter. The process further comprises bonding a plurality of sulfonyl amidite moieties to the hydroxyl groups to form a plurality of cleavable linkers bonded to the known locations. The cleavable linkers comprise a linker hydroxyl moiety and a base-labile cleaving moiety. A phosphorous-oxygen bond is formed between phosphorous of the sulfonyl amidite moieties and oxygen of the hydroxyl groups. The process further comprises synthesizing a plurality of oligomers covalently bound to the linker hydroxyl moiety. The process further comprises cleaving the oligomers from the known locations at the base-labile cleaving moiety using a cleaving base. The oligomers comprise DNA and RNA and have a 3' phosphate after cleaving from the solid surface. The oligomers are oligonucleotides having a 3' phosphate. The pool comprises more than approximately 100 different oligonucleotides.

Further disclosed herein is a microarray having base cleavable sulfonyl linkers. The microarray comprises an array device having a plurality of known locations where each location has a plurality of reacted hydroxyl groups. The density of the plurality of known locations is greater than approximately 100 per square centimeter. The microarray further comprises a plurality of reacted sulfonyl amidite moieties bonded to the plurality of reacted hydroxyl groups to form a plurality of cleavable linkers attached to the plurality of known locations. The cleavable linkers have a linker hydroxyl group and a base-labile cleaving site. A phosphorous-oxygen bond is between phosphorous of the reacted sulfonyl amidite moieties and oxygen of the reacted hydroxyl groups.

Further disclosed herein is a microarray having base cleavable sulfonyl linkers. The microarray comprises an array device having a plurality of known locations where each location has a plurality of reacted hydroxyl groups. The density of the plurality of known locations is greater than approximately 100 per square centimeter. The microarray further comprises a plurality of reacted sulfonyl amidite moieties bonded to the plurality of reacted hydroxyl groups to form a plurality of cleavable linkers attached to the plurality of known locations. The cleavable linkers have a linker hydroxyl group and a base-labile cleaving site. A phosphorous-oxygen bond is between phosphorous of the reacted sulfonyl amidite moieties and oxygen of the reacted hydroxyl groups. The microarray further comprises oligomers bonded to the linker hydroxyl groups.

Further disclosed herein is a process for forming a microarray having cleavable succinate linkers. The process comprises providing a solid surface having free hydroxyl groups at known locations. The density of the known locations is greater than approximately 100 locations per square centimeter. The process further comprises bonding a linker moiety to the hydroxyl groups. The linker moiety comprises free amine group and a hydroxyl bonding group. The process further comprises bonding a succinate-containing moiety having free carboxyl groups to the free amine groups to form cleavable linkers attached to the known locations. The succinate-containing moieties comprise a sugar having both a nucleotide base group and a succinate group bonded to the sugar. The cleavable linkers have a base-labile cleaving site on the succinate group and a reactable hydroxyl group on the sugar group. In one or more embodiments, the sugar moiety has one or a plurality of free hydroxyl groups. In another embodiment, the process further comprises synthesizing oligomers, such as oligonucleotides, attached to free hydroxyl groups of the sugar moiety. In another embodiment, the process further comprises cleaving oligomers at the base-labile cleaving site from the known location using a cleaving base, whereby the oligomers are recoverable.

Further disclosed herein is a microarray having base cleavable succinate linkers. The microarray comprises a solid surface having known locations and reactive hydroxyl groups. The known locations have a density greater than approximately 100 per square centimeter. The microarray further comprises a plurality of reactive amino amidite moieties bonded to the reactive hydroxyl groups on the solid surface. The reactive amino moieties comprise an amine group and a hydroxyl bonding group. The hydroxyl bonding group is bonded to the reactive hydroxyl groups at the known locations. The microarray further comprises a plurality of reactive succinate moieties bonded to the amine groups. The reactive succinate moieties comprise a sugar group bonded to the succinate group and to a base group bonded. In an alternative embodiment, microarray further comprises oligomers bonded onto the reactable hydroxyl groups. In one or more embodiments, the sugar group is ribose and the base group is selected from the group consisting of adenine, guanine, cytosine, and uracyl, or the sugar group is deoxyribose and the base group is selected from the group consisting of adenine, guanine, cytosine, and thymine.

Further disclosed herein is a process of forming a microarray having base cleavable phosphoramidite linkers. The process comprises providing a microarray having a surface with a plurality of known locations on the surface. Each location has a plurality of hydroxyl groups, and the density of the known locations is greater than approximately 100 per square centimeter on the surface. The process further comprises bonding a plurality of base cleavable phosphoramidite linkers to the plurality of hydroxyl groups directly or by using an intermediate chemical moiety attached to the hydroxyl groups to form a plurality of cleavable linkers at the plurality of known locations. The cleavable linkers each have a linker hydroxyl group and a base-labile cleaving site.

The linker hydroxyl group is protected by a protecting group, and the base-labile cleaving site is an ether linkage.

Further disclosed herein is a process of forming a microarray having base cleavable phosphoramidite linkers. The process comprises providing a microarray having a surface with a plurality of known locations on the surface. Each location has a plurality of hydroxyl groups, and the density of the known locations is greater than approximately 100 per square centimeter on the surface. The process further comprises bonding a plurality of base cleavable phosphoramidite linkers to the plurality of hydroxyl groups directly or by using an intermediate chemical moiety attached to the hydroxyl groups to form a plurality of cleavable linkers at the plurality of known locations. The cleavable linkers each have a linker hydroxyl group and a base-labile cleaving site. The linker hydroxyl group is protected by a protecting group, and the base-labile cleaving site is an ether linkage. The process further comprises synthesizing oligomers onto the linker hydroxyl groups to provide a microarray of oligomers. The protecting group is removed from the linker hydroxyl groups before synthesizing the oligomers, and the oligomers at the known locations, as between different known locations, are different or the same.

Further disclosed herein is a process of forming a microarray having base cleavable phosphoramidite linkers. The process comprises providing a microarray having a surface with a plurality of known locations on the surface. Each location has a plurality of hydroxyl groups, and the density of the known locations is greater than approximately 100 per square centimeter on the surface. The process further comprises bonding a plurality of base cleavable phosphoramidite linkers to the plurality of hydroxyl groups directly or by using an intermediate chemical moiety attached to the hydroxyl groups to form a plurality of cleavable linkers at the plurality of known locations. The cleavable linkers each have a linker hydroxyl group and a base-labile cleaving site. The linker hydroxyl group is protected by a protecting group, and the base-labile cleaving site is an ether linkage. The process further comprises synthesizing oligomers onto the linker hydroxyl groups to provide a microarray of oligomers. The protecting group is removed from the linker hydroxyl groups before synthesizing the oligomers, and the oligomers at the known locations, as between different known locations, are different or the same. The process further comprises cleaving at the base-labile cleaving site the oligomers from the surface using a cleaving base to provide a pool of cleaved oligomers.

Further disclosed herein is a pool of oligomers produced according to one or more of the processes disclosed herein, wherein the oligomers are oligonucleotides having a 3' phosphate, wherein the pool comprises more than approximately 100 different oligonucleotides. Further disclosed herein is a pool of oligomers produced according to one or more of the processes disclosed herein, wherein the oligomers are oligonucleotides having a 3' hydroxyl, wherein the pool comprises more than approximately 100 different oligonucleotides.

In one or more embodiments, the oligomers are selected from the group consisting of DNA, RNA, and polypeptides, and combinations thereof. In one or more embodiments, the cleaving base is selected from the group consisting of chemical base, ammonium hydroxide, electrochemically generated base, sodium hydroxide, potassium hydroxide, methylamine, and ethylamine and combinations thereof. In one or more embodiments, the oligomers are synthesized in situ using electrochemical synthesis. In one or more embodiments, the oligomers are synthesized in situ by a method selected from the group consisting of (i) printing reagents via ink jet or other printing technology and using regular phosphoramidite chemistry, (ii) maskless photo-generated acid controlled synthesis and using regular phosphoramidite chemistry, (iii) mask-directed parallel synthesis using photocleavage of photolabile protecting groups, and (iv) maskless parallel synthesis using photo-cleavage of photolabile protecting groups and digital photolithography.

Further disclosed herein is a microarray having base cleavable linkers. The microarray comprises a microarray having a surface with a plurality of known locations on the surface, wherein each location has a plurality of hydroxyl groups, wherein the density of the known locations is greater than approximately 100 per square centimeter on the surface. The microarray further comprises a plurality of base cleavable linkers bonded to the plurality of hydroxyl groups to form a plurality of cleavable linkers at the plurality of known locations, wherein the cleavable linkers each have a linker hydroxyl group and a base-labile cleaving site.

In one or more embodiments, the surface has electrodes and each of the known locations are associated with one of the electrodes, wherein the electrodes are electronically addressable. In one or more embodiments, the known locations are on the same surface as the electrodes, on an opposing surface to the electrodes, or on an overlayer over the electrodes.

In one or more embodiments, the array comprises electrodes and each of the known locations has an electrode, wherein the electrodes are electronically addressable. In one or more embodiments, the known locations are on the same surface as the electrodes, on an opposing surface to the electrodes, or on an overlayer over the electrodes. An example of an electrode microarray is a CombiMatrix CustomArray™ 12K, which has over 12,000 electrodes and an electrode density of approximately 17,778 electrodes per square centimeter.

In one or more embodiments, the oligomers are selected from the group consisting of DNA, RNA, and polypeptide, and combinations thereof.

In one or more embodiments, the oligomers are synthesized in situ using electrochemical synthesis. In one or more embodiments, the oligomers are synthesized in situ by a method selected from the group consisting of (i) printing reagents via ink jet or other printing technology and using regular phosphoramidite chemistry, (ii) maskless photo-generated acid controlled synthesis and using regular phosphoramidite chemistry, (iii) mask-directed parallel synthesis using photo-cleavage of photolabile protecting groups, and (iv) maskless parallel synthesis using photo-cleavage of photolabile protecting groups and digital photolithography.

In one or more embodiments, the array is glass having a silane linking agent having organic hydroxyl groups, wherein the organic hydroxyl groups are the hydroxyl groups of the known locations. Preferably, the silane linking agent is a chemical selected from the group consisting of hydroxymethyltriethoxysilane, N-(3-triethoxysilylpropyl) gluconamide, N-(3-triethoxysilylpropyl)-4-hydroxybutyramide, 1-trimethoxysilyl-3-propanol, 1-trimethoxysilyl-2,3-propanediol, 1-triethoxysilyl-3-propanol, 1-triethoxysilyl-2,3-propanediol, 1-trimethoxysilyl-2-ethanol, triethoxysilyl-2-ethanol, trimethoxysilyl-11-undecanol, and triethoxysilyl-11-undecanol and combinations thereof.

In one or more embodiments, the sulfonyl amidite moiety is 2-[2-(4,4'-dimethoxytrityloxy)ethylsulfonyl)ethyl-(2-cyanoethyl)-(N,N-diisopropyl)-phosphoramidite.

In one or more embodiments, spacers having reactive hydroxyl groups are bound to the hydroxyl moieties, wherein the sulfonyl amidite moieties are bound to the reactive hydroxyl groups of the spacers. Preferably, the spacer is selected from the group consisting of DNA, RNA, polyethylene glycol, and polypeptides, and combinations thereof. Preferably, the spacer is approximately 1 to 35 mers.

In one or more embodiments, a porous reaction layer attached to the known locations provides the hydroxyl groups, wherein the porous reaction layer comprises a chemical species or mixture of chemical specie, wherein the chemical species is selected from the group consisting of monosaccharides, disaccharides, trisaccharides, polyethylene glycol, polyethylene glycol derivative, N-hydroxysuccinimide, formula I, formula II, formula III, formula IV, formula V, formula VI, formula VII, and combinations thereof, wherein formula I is

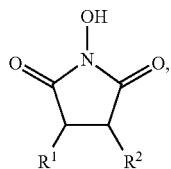

formula II is

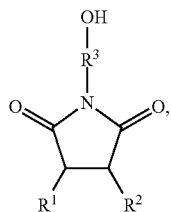

formula III is HOR$^4$(OR$^5$)$_m$R$^9$ formula IV is

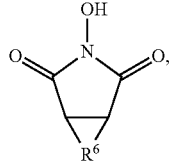

formula V is

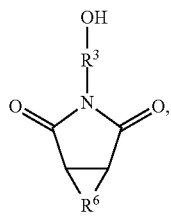

formula VI is

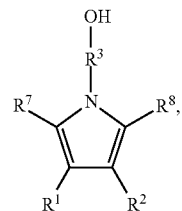

and formula VII is

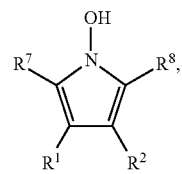

wherein in each formula m is an integer from 1 to 4; R$^1$, R$^2$; R$^7$, and R$^8$ are independently selected from the group consisting of hydrogen, and substituted and unsubstituted alkyl, alkenyl, alkynyl, cycloalkyl, cycloalkenyl, cycloalkynyl, aryl, heterocyclic ring, and polycyclic group, and halo, amide, alkoxy, acyl, acyloxy, oxycarbonyl, acyloxycarbonyl, alkoxycarbonyloxy, carboxy, amino, secondary amino, tertiary amino, hydrazino, azido, alkazoxy, cyano, isocyano, cyanato, isocyanato, thiocyanato, fulminato, isothiocyanato, isoselenocyanato, selenocyanato, carboxyamido, acylimino, nitroso, aminooxy, carboximidoyl, hydrazonoyl, oxime, acylhydrazino, amidino, sulfide, sulfoxide, thiosulfoxide, sulfone, thiosulfone, sulfate, thiosulfate, hydroxyl, formyl, hydroxyperoxy, hydroperoxy, peroxy acid, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, sulfinimidic acid, sulfonimidic acid, sulfinohydrazonic acid, sulfonohydrazonic acid, sulfinhydroximic acid, sulfonohydroximic acid, and phosphoric acid ester; R$^3$ is selected from the group consisting of heteroatom group, carbonyl, and substituted and unsubstituted alkyl, alkenyl, alkynyl, cycloalkyl, cycloalkenyl, cycloalkynyl, aryl, heterocyclic ring, and polycyclic group; R$^4$ and R$^5$ are independently selected from the group consisting of methylene, ethylene, propylene, butylene, pentylene, and hexylene; R$^6$ forming a ring structure with two carbons of succinimide and is selected from the group consisting of substituted and unsubstituted alkyl, alkenyl, alkynyl, cycloalkyl, cycloalkenyl, cycloalkynyl, aryl, heterocyclic ring, and polycyclic group; and R$^9$ is selected from the group consisting of amino and hydroxyl.

In one or more embodiments, the monosaccharide is selected from the group consisting of allose, altrose, arabinose, deoxyribose, erythrose, fructose, galactose, glucose, gulose, idose, lyxose, mannose, psicose, L-rhamnose, ribose, ribulose, sedoheptulose, D-sorbitol, sorbose, sylulose, tagatose, talose, threose, xylulose, and xylose. In one or more embodiments, the disaccharide is selected from the group consisting of amylose, cellobiose, lactose, maltose, melibiose, palatinose, sucrose, and trehalose. In one or more embodiments, the trisaccharide is selected from the group consisting of raffinose and melezitose.

In one or more embodiments, the polyethylene glycol derivative is selected from the group consisting of diethylene glycol, tetraethylene glycol, polyethylene glycol having primary amino groups, 2-(2-aminoethoxy) ethanol, ethanol amine, di(ethylene glycol) mono allyl ether, di(ethylene glycol) mono tosylate, tri(ethylene glycol) mono allyl ether, tri(ethylene glycol) mono tosylate, tri(ethylene glycol) mono benzyl ether, tri(ethylene glycol) mono trityl ether, tri(ethylene glycol) mono chloro mono methyl ether, tri(ethylene glycol) mono tosyl mono allyl ether, tri(ethylene glycol) mono allyl mono methyl ether, tetra(ethlyne glycol) mono allyl ether, tetra(ethylene glycol) mono methyl ether, tetra (ethylene glycol) mono tosyl mono allyl ether, tetra(ethylene glycol) mono tosylate, tetra(ethylene glycol) mono benzyl ether, tetra(ethylene glycol) mono trityl ether, tetra(ethylene glycol) mono 1-hexenyl ether, tetra(ethylene glycol) mono 1-heptenyl ether, tetra(ethylene glycol) mono 1-octenyl ether, tetra(ethylene glycol) mono 1-decenyl ether, tetra (ethylene glycol) mono 1-undecenyl ether, penta(ethylene glycol) mono methyl ether, penta(ethylene glycol) mono allyl mono methyl ether, penta(ethylene glycol) mono tosyl mono methyl ether, penta(ethylene glycol) mono tosyl mono allyl ether, hexa(ethylene glycol) mono allyl ether, hexa (ethylene glycol) mono methyl ether, hexa(ethylene glycol) mono benzyl ether, hexa(ethylene glycol) mono trityl ether, hexa(ethylene glycol) mono 1-hexenyl ether, hexa(ethylene glycol) mono 1-heptenyl ether, hexa(ethylene glycol) mono 1-octenyl ether, hexa(ethylene glycol) mono 1-decenyl ether, hexa(ethylene glycol) mono 1-undecenyl ether, hexa (ethylene glycol) mono 4-benzophenonyl mono 1-undecenyl ether, hepta(ethylene glycol) mono allyl ether, hepta(ethylene glycol) mono methyl ether, hepta(ethylene glycol) mono tosyl mono methyl ether, hepta(ethylene glycol) monoallyl mono methyl ether, octa(ethylene glycol) mono allyl ether, octa(ethylene glycol) mono tosylate, octa(ethylene glycol) mono tosyl mono allyl ether, undeca(ethylene glycol) mono methyl ether, undeca(ethylene glycol) mono allyl mono methyl ether, undeca(ethylene glycol) mono tosyl mono methyl ether, undeca(ethylene glycol) mono allyl ether, octadeca(ethylene glycol) mono allyl ether, octa(ethylene glycol), deca(ethylene glycol), dodeca(ethylene glycol), tetradeca(ethylene glycol), hexadeca(ethylene glycol), octadeca(ethylene glycol), benzophenone-4-hexa(ethylene glycol) allyl ether, benzophenone-4-hexa(ethylene glycol) hexenyl ether, benzophenone-4-hexa(ethylene glycol) octenyl ether, benzophenone-4-hexa(ethylene glycol) decenyl ether, benzophenone-4-hexa(ethylene glycol) undecenyl ether, 4-fluorobenzophenone-4'-hexa(ethylene glycol) allyl ether, 4-fluorobenzophenone-4'-hexa(ethylene glycol) undecenyl ether, 4-hydroxybenzophenone-4-hexa(ethylene glycol) allyl ether, 4-hydroxybenzophenone-4-hexa(ethylene glycol) undecenyl ether, 4-hydroxybenzophenone-4'-tetra(ethylene glycol) allyl ether, 4-hydroxybenzophenone-4'-tetra(ethylene glycol) undecenyl ether, 4-morpholinobenzophenone-4'-hexa(ethylene glycol) allyl ether, 4-morpholinobenzophenone-4'-hexa(ethylene glycol) undecenyl ether, 4-morpholinobenzophenone-4'-tetra(ethylene glycol) allyl ether, and 4-morpholinobenzophenone-4'-tetra(ethylene glycol) undecenyl ether. Preferably, the polyethylene glycol has a molecular weight of approximately 1,000 to 20,000.

In one or more embodiments, the sugar group is ribose and the nucleotide base group is selected from the group consisting of adenine, guanine, cytosine, and uracyl, or the sugar group is deoxyribose and the base group is selected from the group consisting of adenine, guanine, cytosine, and thymine.

In one or more embodiments, the cleaving base is selected from the group consisting of ammonium hydroxide, electrochemically generated base, sodium hydroxide, potassium hydroxide, methylamine, and ethylamine and combinations thereof, whereby the oligomers comprising DNA and RNA have a 3' hydroxyl after cleaving from the solid surface.

In one or more embodiments, the amino moiety is selected from the group consisting of aminopropyltrimethoxysilane, aminopropyltriethoxysilane, aminopropylmethyldiethoxysilane, aminopropylmethyldiethoxysilane hydrozylate, m-aminophenyltrimethoxysilane, phenylaminopropyltrimethoxysilane, 1,1,2,4-tetramethyl-1-sila-2-azacyclopentane, aminoethylaminopropyltrimethoxysilane, aminoethylaminopropyltrimethoxysilane, aminoethylaminopropyltriethoxysilane, aminoethylaminopropylmethyldimethoxysilane, aminoethylaminopropyltrimethoxysilane hydrolyzate, aminoethylaminoisobutylmethyldimethoxysilane, aminoethylaminoisobutylmethyldimethoxysilane, aminoethylaminoisobutylmethyldimethoxysilane hydrolyzate, trimethoxysilylpropyldiethylenetriamine, vinylbenzylethylenediaminepropyltrimethoxysilane monohydrochloride, vinylbenzylethylenediaminepropyltrimethoxysilane, benzylethylenediaminepropyltrimethoxysilane monohydrochloride, benzylethylenediaminepropyltrimethoxysilane, and allylethylenediaminepropyltrimethoxysilane monohydrochloride, and combinations thereof.

In one or more embodiments, the amino moieties are an amino amidite moiety selected from the group consisting of 3-(trifluoroacetylamino)propyl-(2-cyanoethyl)-N,N-diisopropyl)-phosphoramidite, 2-[2-(4-monomethoxytrityl)aminoethoxy]ethyl-(2-cyanoethyl)-N,N-diisopropyl)-phosphoramidite, 6-(4-monomethoxytritylamino)hexyl-(2-cyanoethyl)-N,N-diisopropyl)-phosphoramidite, 12-(4-monomethoxytritylamino)dodecyl-(2-cyanoethyl)-N,N-diisopropyl)-phosphoramidite, and 6-(trifluoroacetylamino) hexyl-(2-cyanoethyl)-N,N-diisopropyl)-phosphoramidite, and combinations thereof.

In one or more embodiments, the succinate moieties are selected from a salt of a chemical selected from the group consisting of 5'dimethoxytrityl-N-benzoyl-2'-deoxycytidine-3'-O-succinate, 5'dimethyoxytrityl-N-isobutyryl-2'-deoxyguanosine-3'-O-succinate, 5'-dimethoxytrityl-thymidine-3'-O-succinate, and 5'-dimethoxytrityl-N-benzoyl-2'-deoxyadenosine-3'-O-succinate, and combinations thereof. Preferably the salt is a pyridium salt of the succinate moieties.

Figure 1B:
Figure 2:
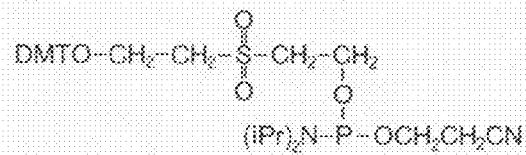
FIG. 2 is a schematic of a sulfonyl amidite used to form a cleavable linker on a micro array.

FIGS. 1A and 1B provide a sequence of drawings that show a process of making the microarrays recited In one or more embodiments; the figures are not drawn to scale. The figures show a cross-section of only one of the plurality of known locations, preferably located on a solid surface of the microarray. Preferably, the density of the plurality of known locations is greater than 100 per square centimeter and can be approximately 1,000 to approximately 1,000,000 locations per square centimeter or even higher. The first step in FIG. 1A shows the hydroxyl groups before reaction. The hydroxyl groups are preferably accessible for chemical reactions thereto. The second step of FIG. 1A shows the sulfonyl amidite moieties attached to the hydroxyl groups through a phosphorous-oxygen bond between the phosphorous of the sulfonyl amidite moieties and the oxygen of the hydroxyl groups. A sulfonyl amidite moiety is shown in FIG. 2. To attach the sulfonyl amidite moiety, a mixture of activator and the amidite is made and applied to the microarray. Preferably, the activator is tetrazole at a concentration of about 0.45 molar before mixing. More preferably, the activator is 5-ethylthio-1H-tetrazole at a concentration of about 0.25 molar before mixing. Preferably, the activator is in acetonitrile. Preferably, the concentration of the amidite is 100 millimolar before mixing. Preferably, the mixture is a one to one mixture by volume. Preferably, the reaction of the amidite proceeds for about 1 to 30 minutes, and more preferably the reaction proceeds for about 5 minutes. After reaction, the hydroxyl groups are referred to as reacted hydroxyl groups. The phosphorous is oxidized from phosphorous III to V according to standard phosphoramidite synthesis. Preferably, the oxidation is performed using Ox-T solution and the reaction proceeds for about 10 to 60 seconds, and more preferably the reaction proceeds for about 30 seconds. The hydroxyl groups that are not reacted are capped. The protecting group on the oxygen of the sulfonyl amidite moieties is removed using acidic reagent. Preferably, acidic reagent is generated electrochemically while being confined by scavenging agents or buffers, natural diffusion, and the porous reaction layer, which partially physically limits diffusion. The protecting group is preferably dimethoxytrityl (DMT) although, generally, any acid-labile protecting group will work such as those disclosed in Montgomery I, II, or III. The resulting structure forms cleavable linkers attached to the microarray at known locations. The cleaving point is shown in the last step of FIG. 1A. FIG. 1B shows an oligonucleotide cleaved from the microarray and having a three prime phosphate.

FIG. 1A shows the attachment of the oligomers after synthesis onto the deprotected hydroxyl of the sulfonyl amidite moieties. Preferably, the oligomers are selected from the group consisting of DNA, RNA, and polypeptide, and combinations thereof. FIGS. 1A and 1B show the oligomers as oligonucleotides. More preferably, the oligomers are DNA. Preferably, the oligomers are synthesized in situ using electrochemical synthesis. Electrochemical synthesis of DNA or RNA uses standard phosphoramidite synthesis and electrochemical deblocking, which is electrochemical generation of acid for deprotection of each unit of a DNA or RNA strand. Electrochemical deblocking involves turning on an electrode to generate acidic conditions at the electrode sufficient to remove the protecting group only at that electrode. The acidic reagent may be confined as disclosed previously for removing DMT on a sulfonyl amidite and as disclosed in the Montgomery patents. Removal of the protecting group allows addition of the next unit (mer). Optionally, the oligomers are synthesized in situ by a method selected from the group consisting of (i) printing reagents via ink jet or other printing technology and using regular phosphoramidite chemistry, (ii) maskless photo-generated acid controlled synthesis and using regular phosphoramidite chemistry, (iii) mask-directed parallel synthesis using photo-cleavage of photolabile protecting groups, and (iv) maskless parallel synthesis using photo-cleavage of photolabile protecting groups and digital photolithography.

Preferably, the cleaving base is selected from the group consisting of ammonium hydroxide, electrochemically generated base, sodium hydroxide, potassium hydroxide, methylamine, and ethylamine and combinations thereof. More preferably, the cleaving base is concentrated ammonium hydroxide, the reaction temperature is about 65 degrees Celsius, and the reaction time is about four to six hours. During exposure to the cleaving base, cleaving occurs as well as deprotection of oligonucleotides synthesized on the cleavable linker. To recover oligonucleotides cleaved from a microarray, the microarray is preferably place on ice for about 10 minutes, and if ammonium hydroxide is used, a vacuum evaporator is used to remove the ammonium hydroxide from the oligonucleotides. The oligonucleotides may be re-suspended into solution and cleaned to remove impurities.

Preferably, each of the known locations is associated with an electrode to form an electrode array, wherein the electrodes are electronically addressable. An example of an electrode microarray is a CombiMatrix CustomArray™ 12 k, which has over 12,000 electrodes and an electrode density of approximately 17,778 electrodes per square centimeter. Preferably, the known locations are on the same surface as the electrodes, on an opposing surface to the electrodes, or on an overlayer over the electrodes.

Optionally, the array comprises a surface that is glass without a silane linking agent or with a silane linking agent. Preferably, the silane linking agent has organic hydroxyl groups that are the hydroxyl groups of the known locations. Preferably, the silane linking agent is a chemical selected from the group consisting of hydroxymethyltriethoxysilane, N-(3-triethoxysilylpropyl)gluconamide, N-(3-triethoxysilylpropyl)-4-hydroxybutyramide, 1-trimethoxysilyl-3-propanol, 1-trimethoxysilyl-2,3-propanediol, 1-triethoxysilyl-3-propanol, 1-triethoxysilyl-2,3-propanediol, 1-trimethoxysilyl-2-ethanol, triethoxysilyl-2-ethanol, trimethoxysilyl-11-undecanol, and triethoxysilyl-11-undecanol and combinations thereof.

Preferably, the sulfonyl amidite moiety is 2-[2-(4,4'-dimethoxytrityloxy)ethylsulfonyl) ethyl-(2-cyanoethyl)-(N,N-diisopropyl)-phosphoramidite. Optionally, spacers having reactive hydroxyl groups are bound to the hydroxyl groups of the known locations, wherein the sulfonyl amidite moities are bound to the reactive hydroxyl groups of the spacers. Preferably, the spacer is selected from the group consisting of DNA, RNA, polyethylene glycol, and polypeptides, and combinations thereof. Preferably, the spacer is approximately 1 to 35 mers. More preferably, the spacer is a 10-T, although A, C, G, or U may be used in the spacer. The T-spacer is convenient because of a lack of a protecting group on the base. An oligonucleotide space may be synthesized using electrochemical synthesis or one of the other methods suitable for oligonucleotide synthesis on a microarray. Final deprotection of an oligonucleotide linker may be accomplished by using electrochemical generation of acid or by exposure to acidic solution such as Deblock-T solution, which is 3% trichloroacetic acid in dichloromethane.

Figure 5A:
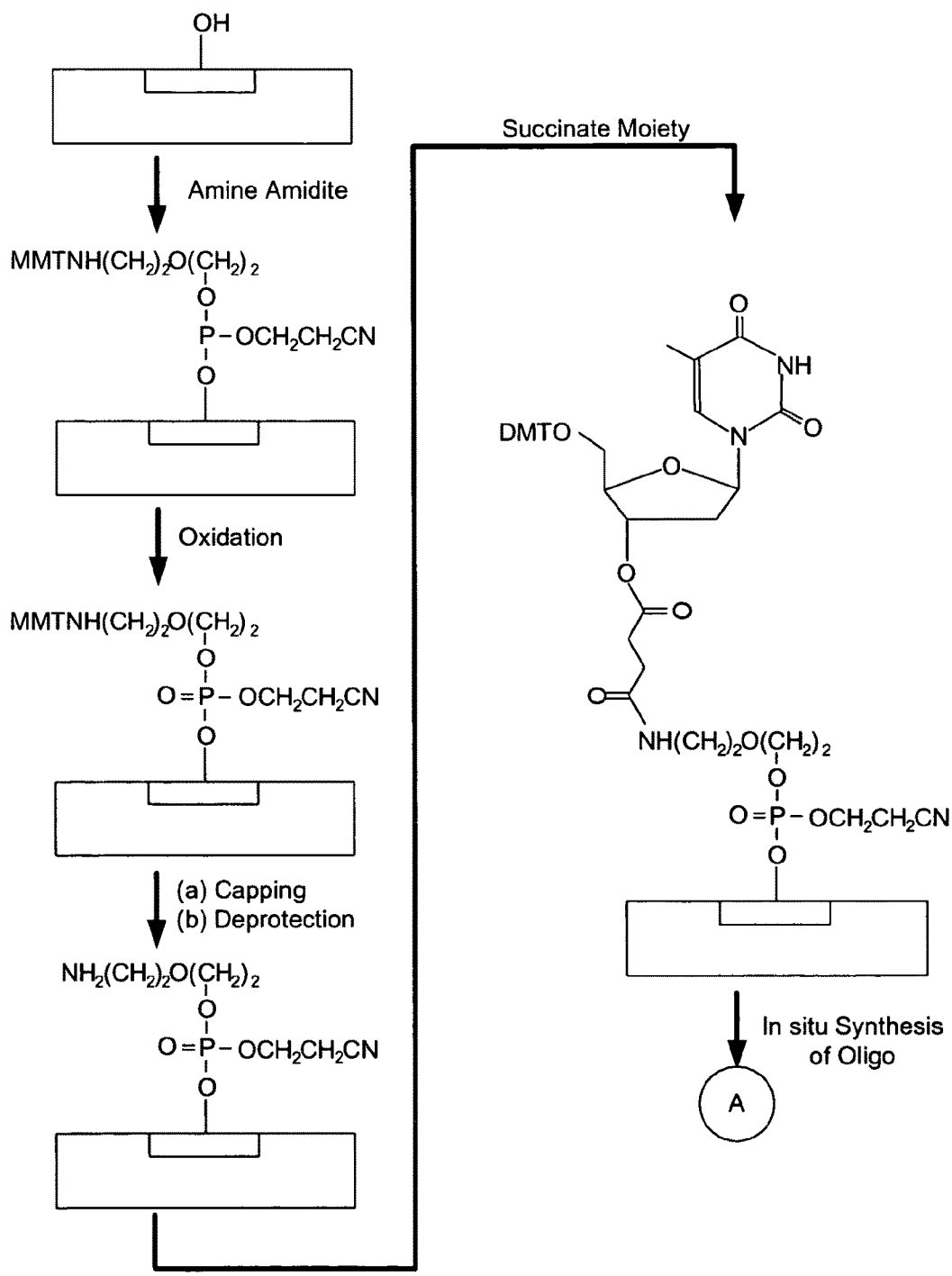
FIGS. 5A and 5B are schematics showing the construction of the microarray of the present invention.
Figure 5B:
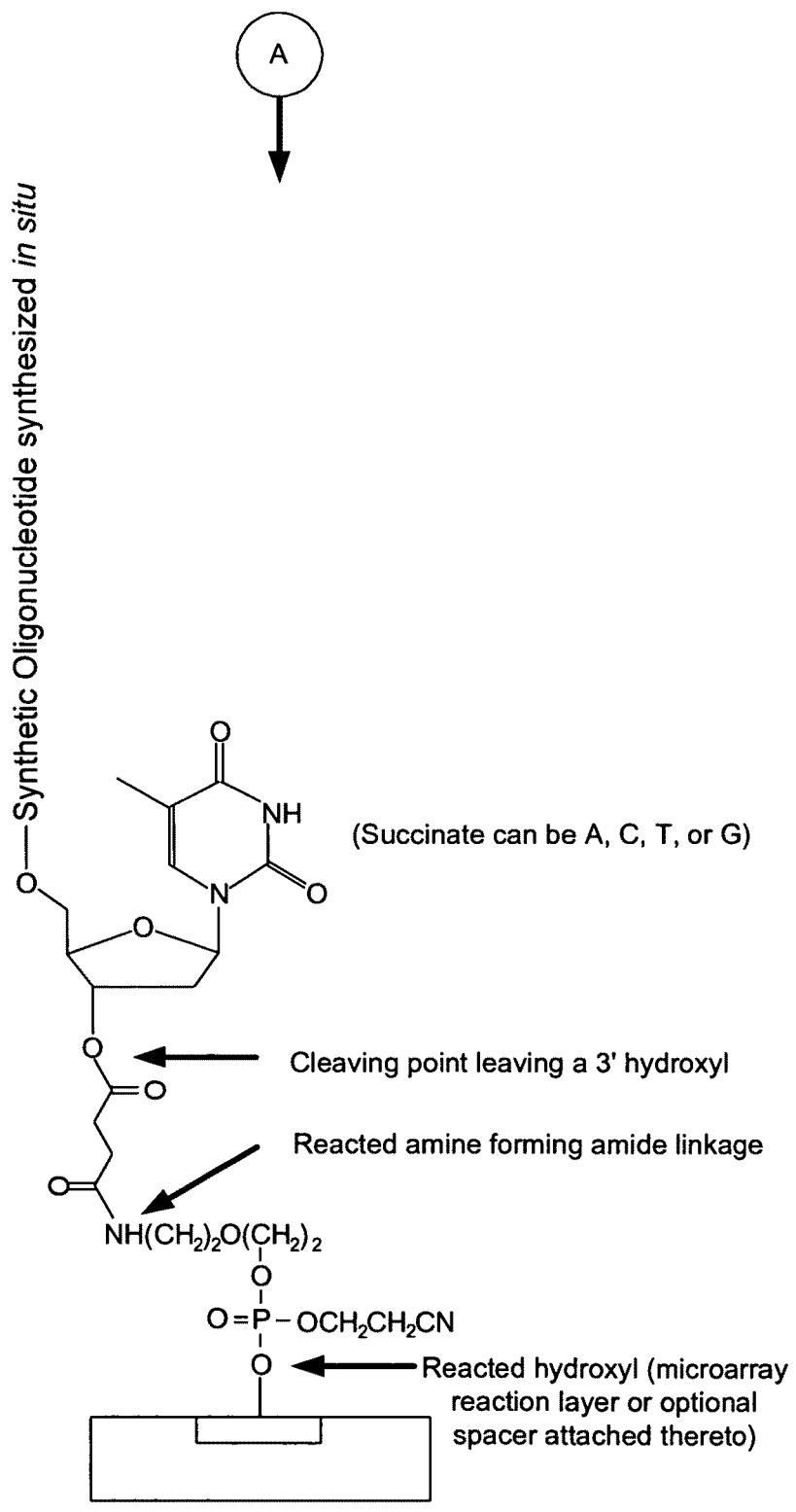

FIGS. 5A and 5B provide a schematic of the construction of a microarray for one or more of the embodiments. The microarray has a solid surface with known locations that have hydroxyl groups. The hydroxyl groups are shown in FIG. 5A in the first step as not reacted; however, the second step shows the hydroxyl groups reacted. The density of the known locations is greater than approximately 100 locations per square centimeter. Density of the known locations can be approximately 1,000 to 1,000,000 locations per square centimeter. Only one known location with one hydroxyl is shown. Amino moieties are attached to the hydroxyl groups. The attachment is through a phosphorous-oxygen bond between the phosphorous of amino amidite moieties and the oxygen of the hydroxyl groups as shown in the second step of FIG. 5A. Generally, the hydroxyl groups are referred to as reacted hydroxyl groups after attachment of the amino moieties. The amino moieties have an amine group and a hydroxyl reactive group. The hydroxyl reactive group bonds to the hydroxyl groups at the known locations.

The succinate moieties are attached to the amino moieties through amide bonds as shown in the last step in FIG. 5A. Prior to attachment of the succinate, the microarray is capped to cap unreacted hydroxyl groups followed by deprotection to remove the protecting group on the amine. The protecting group is preferably monomethoxytrityl (MMT) although, generally, any acid-labile protecting group will work such as those disclosed in Montgomery I, II, or III, including dimethoxytrityl (DMT). The resulting structure forms cleavable linkers attached to the microarray. The cleaving point is shown in FIG. 5B. Oligomers are attached to the cleavable linkers as shown in FIG. 5B. If the oligomers are DNA or RNA and cleaved from the microarray, the resulting oligonucleotide has a 3' hydroxyl. FIG. 5B provides an example structure on a microarray. The succinate moieties have a succinate group bonded to a sugar group and a base bonded to the sugar group.

The amine group on the amino amidite moiety is protected by a protecting group. Generally, amino amidite moieties bonded to the surface are referred to as reacted amino amidite moieties. Such protection groups must be removed before a succinate moiety can be reacted to form an amide linkage between the amino amidite and the succinate moiety. The protecting groups are removed on an electrode microarray by the generation of acidic protons at the locations associated with an activated electrode. Alternatively, acidic solution may be used. Alternatively, photolabile protecting groups on the amine may be used such as those disclose in Fodor (cited previously).

Figure 6:
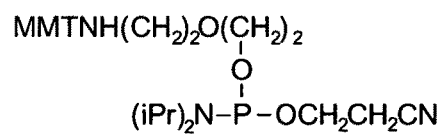
FIG. 6 provides exemplary compounds used to construct the microarray of the present invention.
Figure 6:
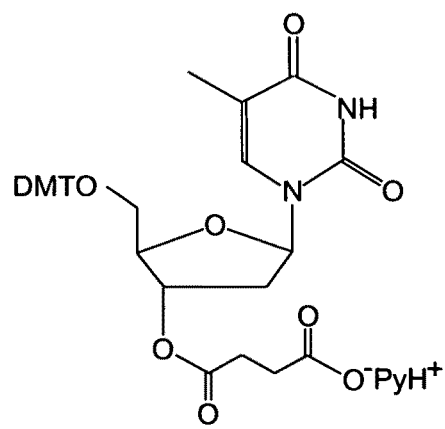

In one or more embodiments, succinate moieties reacted to the amino amidite moieties are referred to as reacted succinate moieties. In one or more embodiments, the salt is a pyridinium salt as shown in FIG. 6, Compound B. Other salts of the succinate moieties may be used such as triethyl ammonium salt (Pierce Chemical Company), lutidine salt, or imidizole salt and salts having the form HN(R1R2R3)+, wherein R1, R2, and R3 are alkyl groups. HBTU/HOBT activation of the succinate moiety is a preferred embodiment. Other procedures to activate the succinate can be used and include use of a carbodiimide such as N,N'-dicyclohexyl carbodiimide (DCC) or diisopropylcarbodiimide (DIC) with or without N-hydrooxybenzotriazole (HOBt) or by forming a symmetrical anhydride. Use of other peptide coupling reagents such as 2-(1H-benzotriazole-1-yl)-1,1,3,3-tetramethyluronium tetrafluoroborate (TBTU), 2-(5-norbornene-2,3-dicarboximido)-1,1,3,3-tetramethyluronium tetrafluoroborate (TNTU), O—(N-succinimidyl)-1,1,3,3-tetramethyluronium tetrafluoroborate (TSTU), benzotriazole-1-yl-oxy-tris-(dimethylamino)-phosphoniumhexafluorophasphate (BOP), benzotriazole-1-yl-oxy-tris-pyrrolidino-phosphonium hexafluorophosphate (PyBOP), bromo-tris-pyrrolidino-phosphonium hexafluorophosphate (PyBroP), or 1,1'-carbonyl-diimidazole (CDI).

In one or more embodiments, oligomers are synthesized in situ using electrochemical synthesis. Electrochemical synthesis of DNA uses standard phosphoramidite chemistry coupled with electrochemical deblocking of the protecting groups on the synthesized DNA for the addition of each nucleotide contained in the oligonucleotide. For attachment of the phosphoramidites, the microarray has hydroxyl groups that allow attachment of the first phosphoramidite. Electrochemical deblocking involves turning on an electrode to generate acidic conditions that are sufficient to remove the protecting group only at the active electrode. Buffer in the solution used for deblocking and natural diffusion prevents deblocking at non-activated electrodes. Removal of the protecting groups allows addition of the next phosphoramidite.

Example 1

In this example, a CombiMatrix CustomArray™ 12 k microarray was used to synthesize DNA attached to the microarray through a 10-T spacer and a base-cleavable sulfonyl linker. The microarray had approximately 12,000 platinum electrodes on a solid surface having a porous reaction layer. Each electrode was electronically addressable via computer control. The DNA was electrochemically synthesized in situ onto known locations associated with the electrodes on the microarray. The known locations were on and within a porous reaction layer over the electrodes. The porous reaction layer was composed of sucrose. The electrochemical synthesis used phosphoramidite chemistry coupled with electrochemical deblocking of the protecting groups on the synthesized DNA for the addition of each subsequent nucleotide. For bonding of the phosphoramidites, the microarray had reactive hydroxyl groups provided by the sucrose. Electrochemical deblocking involved turning on an electrode to generate acidic conditions at the electrode that were sufficient to remove the protecting group only at the active electrode. Buffer in the solution used for deblocking and natural diffusion prevented deblocking at non-activated electrodes. Removal of the protecting group allowed addition of the next phosphoramidite.

The cleavable linker was at the end of the 10-T linker/spacer. The microarray was prepared by electrochemical synthesis of the 10-T linker on all locations on the microarray. The final trityl on the 10-T linker was removed using electrochemically-generated acid. After synthesis of the linker and removal of the protecting groups on the linker, a solution having sulfonyl amidite was coupled to selected locations. The sulfonyl amidite was 2-[2-(4,4'-dimethoxytrityloxy) ethylsulfonyl)ethyl-(2-cyanoethyl)-(N,N-diisopropyl)-phosphoramidite. The coupling solution comprised a 1:1 mixture of activator solution and 100 mM sulfonyl amidite solution in acetonitrile. The solution was added to a reaction chamber of the microarray immediately after mixing the components. Care was taken to prevent water contamination during the coupling step. The coupling reaction proceeded for 5 minutes. The reaction chamber was evacuated, and an oxidation solution (Ox-T) was injected and allowed to react for 30 seconds to convert phosphorus III to phosphorus V. The reaction chamber was then cleaned thoroughly with acetonitrile.

A pool of DNA was synthesized onto the cleavable linkers. After synthesis, the microarray was placed in a custom chamber and exposed to ammonium hydroxide at 65° C. for 4-6 hours. The chamber was designed to be able to withstand the pressures created by heating the solution up to the temperature. During this step, the oligonucleotides were cleaved from the microarray and deprotected as the same time.

The microarray was placed on ice for about 10 minutes to allow the ammonium hydroxide to cool to prevent the solution from spraying out of the chamber because of the relatively higher pressure inside the chamber. The ammonium hydroxide solution, which contained the target oligonucleotides, was placed in a 65-microliter tube using a pipette. The ammonium hydroxide was removed using a SpeedVac® vacuum system at a temperature of about 65-85° C. until dry, which took about 30 minutes to an hour. The oligonucleotides were in the form of a pellet at the bottom of the tube. The oligonucleotides were resuspended in a Tris buffer solution and then cleaned using a Microspin® G-25 column obtained from Amersham.

Example 2

Thirteen microarrays were prepared according to Example 1 but with some exceptions. First, the microarrays had the same oligonucleotide sequence synthesized on each electrode rather than a pool of oligonucleotides. Additionally, six of the microarrays had the sulfonyl cleavable linker, and seven of the microarrays did not have the sulfonyl cleavable linker.

After synthesis of the oligonucleotides on the group of six microarrays having the cleavable linker, each of those microarrays was exposed to a concentrated ammonium hydroxide solution for four hours at 65 degrees Celsius to remove the oligonucleotides. The oligonucleotides from each microarray were recovered and amplified using PCR. The oligonucleotide recovery was quantified using quantitative PCR, which used SYBR I as the fluorescent intercalating dye. The fluorescence intensity (FI) was monitored during PCR and plotted against the number of PCR cycles. The FI for each reaction was normalized to the highest FI value. For each reaction, the FI value at 50% of the maximum FI value was calculated for each microarray, and the corresponding number of PCR cycles was obtained by interpolation. The average number of PCR cycles to reach 50% FI value for the group six microarrays was about 11 cycles.

For the group of seven microarrays without the cleavable linker, each of those microarrays was exposed to different treatments in an attempt to remove the oligonucleotides for comparison to the cleavable linker microarrays. The treatments included 1% hydrogen peroxide, 1% hydrogen peroxide plus 0.2 molar sucrose, 0.1 molar hydrochloric acid, 0.4 molar hydrochloric acid, concentrated ammonium hydroxide, and methylamine. The oligonucleotides from each microarray were recovered and amplified using PCR. The fluorescence intensity (FI) was monitored during PCR and plotted against the number of PCR cycles. The FI was normalized to the highest FI value. The FI value at 50% of the maximum FI value was calculated for each microarray, and the corresponding number of PCR cycles was obtained by interpolation. The range of the number of PCR cycles to reach 50% FI value for the group seven microarrays was from about 27 cycles to about 35 cycles. Quantitative comparison of the recovery of oligonucleotides from microarrays with and without the cleavable linkers using a standard curve made from commercially synthesized oligonucleotides (of identical sequence) revealed that the microarrays having the cleavable linker yielded an increased recovery of approximately six orders of magnitude over any other removal method we used.

Example 3

Figure 3:
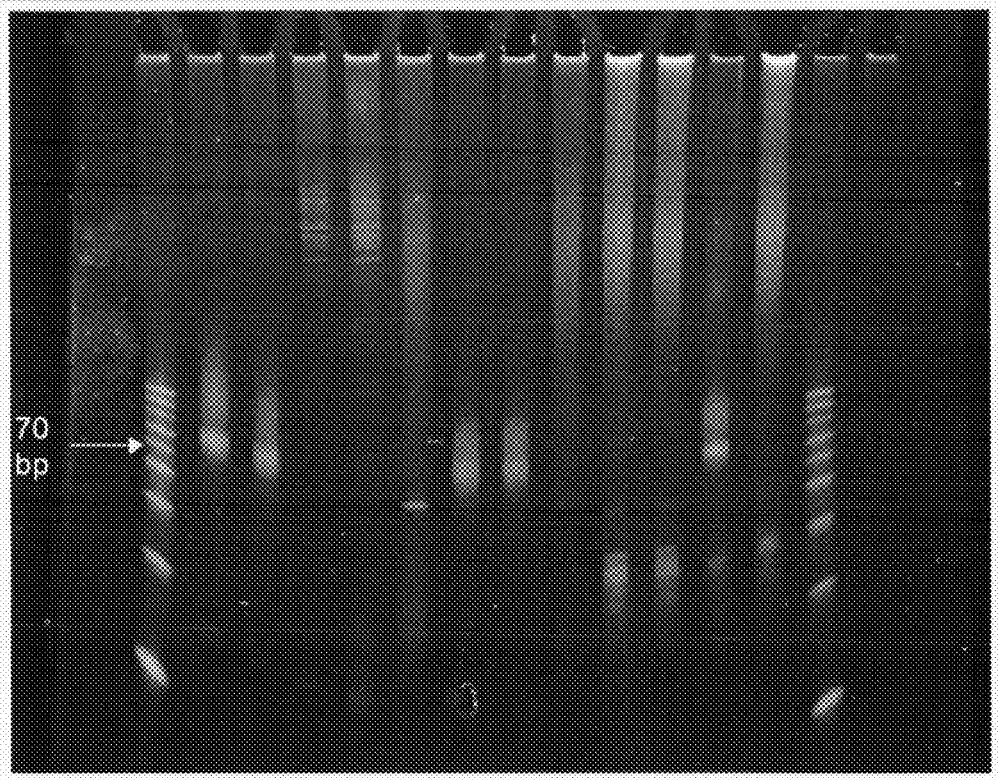
FIG. 3 is an image of a gel from a gel electrophoresis of oligonucleotides recovered from three different microarrays having the cleavable sulfonyl linker.

In this example, three different electrode microarrays were synthesized with each having different oligonucleotides ranging from 66 to 80 base pairs. Each microarray was prepared as in Example 1 except for the different oligonucleotides. After synthesis, the microarrays were exposed to concentrated ammonium hydroxide solution for four hours at 65 degrees Celsius to remove the oligonucleotides. The oligonucleotides from each microarray were recovered. The recovered oligonucleotides were amplified using PCR. The amplified oligonucleotides were subjected to gel electrophoresis. The gel was a 20% polyacrylamide gel. The electrophoresis conditions were 200 volts for 90 minutes. The expected PCR product was 66 to 80 base pairs. FIG. 3 shows an image of the electrophoresis gel. Oligonucleotides 321/322 were from the first microarray. Oligonucleotides 323/324 were from the second microarray. Oligonucleotides 325/326 were from the third microarray. The lanes having a positive sign are those where the oligonucleotides were expected to be located. The lanes having a negative sign are those where the oligonucleotides were not expected to be located. Thus, the olignucleotideos were cleaved from the microarray as expected.

Example 4

In this example, a CombiMatrix CustomArray™ 12K microarray was used to synthesize oligonucleotides attached to the microarray through a base-cleavable linker. The microarray had approximately 12,000 platinum electrodes on a solid surface having a porous reaction layer, wherein each electrode was electronically addressable via computer control. The oligonucleotides were DNA and were synthesized in situ using electrochemical synthesis at locations associated with the electrodes on the microarray. Electrochemical synthesis used standard phosphoramidite chemistry coupled with electrochemical deblocking of the protecting groups on the synthesized DNA for the addition of each nucleotide contained in the oligonucleotide. For attachment of the phosphoramidites, the microarray had organic reactive hydroxyl groups that allowed attachment of the first phosphoramidite. Electrochemical deblocking involved turning on an electrode to generate acidic conditions at the electrode that were sufficient to remove the protecting group only at the active electrode. Buffer in the solution used for deblocking and natural diffusion prevented deblocking at non-activated electrodes. Removal of the protecting group allowed addition of the next phosphoramidite.

Some electrodes were used as controls while some electrodes were used to synthesize the oligonucleotides. At the non-control locations, a 15-unit deoxythymidylate spacer was synthesized on the reactive hydroxyl groups. At some but not all non-control locations, an amine amidite obtained from Glen Research was attached to the 15-unit spacer. The specific amine amidite was 2-[2-(4-Monomethoxytrityl) aminoethoxy]ethyl-(2-cyanoethyl)-N,N-diisopropyl)-phosphoramidite, catalog number 10-1905-xx (5'-Amino-Modifier 5.) The amine amidite had monomethoxytrityl (MMT) protecting groups on the amine. The MMT protecting groups were removed using electrochemical generation of acid by activating selected electrodes.

After removal of the MMT protecting groups, the amine was reacted to a T-succinate to form an amide linkage between the amine groups and the succinate. The specific T-succinate used was 5'-dimethyloxytrityl-thymidine-3'-O-succinate (pyridium salt) obtained from Transgenomic. (Alternatively, A, C, G, succinates could have been used.) The solution to attach the T-succinate to the amine was made by adding 330 milligrams of T-succinate, 150 milligrams of O-benzotriazol-1-yl-N,N,N',N'-tetramethyluronium hexafluorophosphate (HBTU), and 60 milligrams of N-hydroxybenztriazole (HOBT) to one milliliter dimethyl formamide(DMF). To this solution, 225 microliters of diisopropylethylamine (DIEPA) was added and the resulting mixture was vortexed to dissolve the material (total mixing time 5-10 min) prior to use.

To attach the T-succinate, the microarray was placed in a manifold, rinsed with anhydrous DMF, and exposed to one-half of the T-succinate coupling mixture for one hour at room temperature. The microarray was washed in the manifold using different solvents successively as follows: 5 milliliters of DMF, 5 milliliters of methylene chloride, and 5 milliliter of DMF. The microarray was exposed to the second half of the coupling mixture for one hour at room temperature. After the completion of the second exposure to the T-succinate reaction mixture, the microarray was washed again using the same washing as above followed by methylene chloride (5 ml) and a stream of ethanol from a squirt bottle. After washing, the microarray was ready for electrochemical synthesis. Synthesis was done on a CombiMatrix bench top synthesizer, wherein oligonucleotides of three different lengths (37, 42, and 47 bp) were synthesized.

After the completion of electrochemical synthesis, the synthetic oligonucleotides on the microarray were deprotected and cleaved by exposure to concentrated ammonium hydroxide in a pressurized cell at 65° C. The concentration of ammonium hydroxide was 28-30%. During this deprotection step, the cleavable succinate linkage was cleaved thus releasing the synthetic oligonucleotides. The oligonucleotides were isolated by evaporating the ammonia solution and were subjected to amplification using polymerase chain reaction (PCR). The oligonucleotides could be amplified with one set of PCR primers due to the presence of primer amplification sites at the ends of the oligonucleotides. The oligonucleotides were dissolved in 75 microliters of Tris buffer at 95° C. for 5 minutes.

Figure 7:
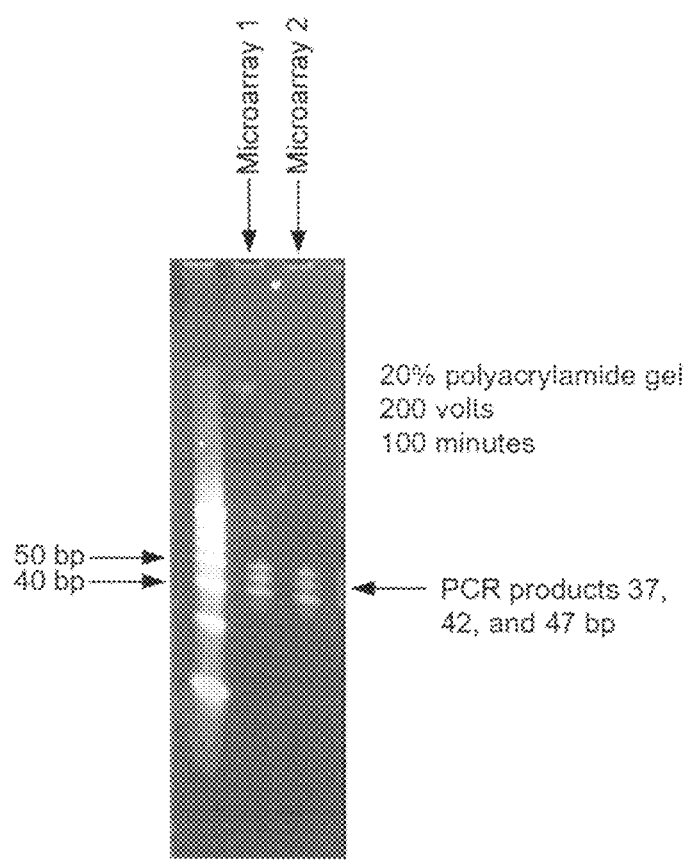
FIG. 7 provides an image of the results from gel electrophoresis of DNA strands that were amplified by PCR. The image shows recovery of the three different DNA strands from a microarray after cleaving the strands from a cleavable linker. The DNA strands were synthesized in situ using electrochemical synthesis on the cleavable linker attached to the microarray.

To test if the nucleotides were released, a series of PCR reactions were performed to determine if the oligonucleotides were present in solution. PCR reaction products were run on a non-denaturing polyacrylamide gel (20%) for 100 minutes at 200 volts. When the separation of the PCR products was complete, the gel was stained with SYBR green II dye to visualize the PCR product as shown in FIG. 7. Separation of the PCR product by gel electrophoresis revealed that all three products (37, 42, and 47 bp) were present in approximately equal amounts and ran at the calculated molecular weight. The novel linker allowed for the release of oligonucleotides from the microarray surface.

Figure 4:
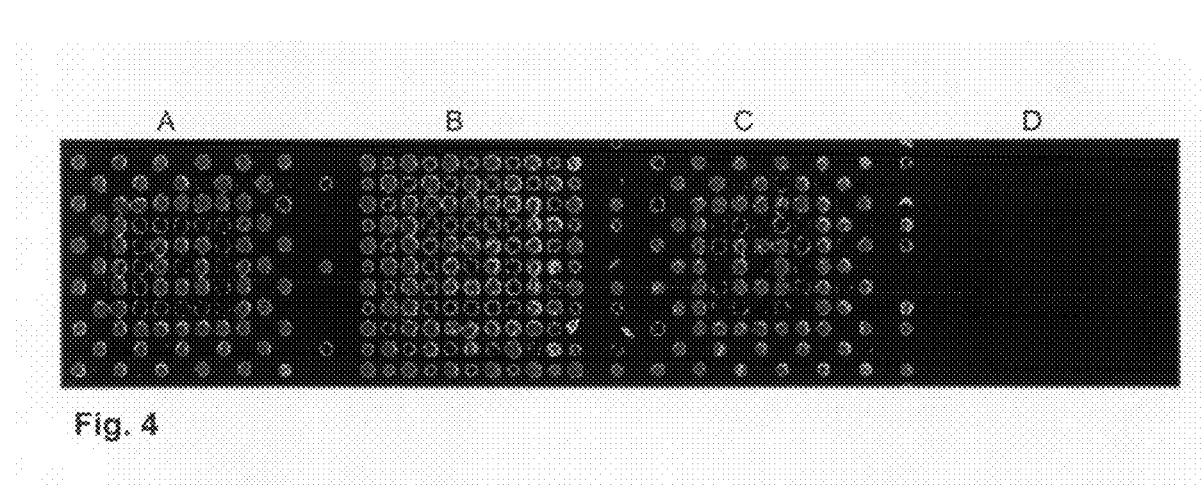
FIG. 4 shows an image of a portion of the microarray after exposure to the fluorescently labeled oligonucleotide. There are four different areas, A, B, C, and D, shown in the figure. In areas A, B, and C, oligonucleotides were synthesized with and without a cleavable linker. As can be seen in the figure, the microarray locations having the cleavable linker between the oligonucleotide and the microarray are dark, indicating little or no hybridizable oligonucleotide remained after cleaving. In contrast, those locations that did not have the cleavable linker between the oligonucleotide and the microarray are brighter, which indicates that the oligonucleotide remained on the microarray. In area D, some electrodes had cleavable linker while others did not; however, no oligonucleotides were synthesized so that the entire area appears dark.

At some locations on the array, the oligonucleotides synthesized were attached without the cleavable linker. Thus, oligonucleotides attached without the cleavable linker would be expected to remain on the microarray after the ammonium hydroxide reaction. To determine whether there were oligonucleotides remaining on the microarray after the ammonium hydroxide reaction, the microarray was exposed to complementary oligonucleotides having a fluorescent label. FIG. 4 shows an image of a portion of the microarray after exposure to the fluorescently labeled oligonucleotide. There are four different areas, A, B, C, and D, shown in the figure. In areas A, B, and C, oligos were synthesized with and without the cleavable linker. As can be seen in the figure, the microarray locations having the cleavable linker between the oligonucleotide and the microarray are completely dark or are mostly dark indicating little or no DNA remains after cleaving. In contrast, those locations that did not have the cleavable linker between the oligonucleotide and the microarray are brighter, which indicates that the oligonucleotide remained on the microarray. In area D, some electrodes had cleavable linker while some did not; however, no oligo was synthesized so that the entire area appears dark.

In an embodiment of the invention, a process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage.

In an embodiment of the invention, a process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same.

In an embodiment of the invention, a process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same, and cleaving at the base-labile cleaving site the oligomers from the surface using a cleaving base to provide a pool of cleaved oligomers.

In an embodiment of the invention, a process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same, and cleaving at the base-labile cleaving site the oligomers from the surface using a cleaving base to provide a pool of cleaved oligomers, wherein the oligomers are selected from the group consisting of DNA, RNA, and polypeptides, and combinations thereof.

In an embodiment of the invention, a process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same, and cleaving at the base-labile cleaving site the oligomers from the surface using a cleaving base to provide a pool of cleaved oligomers, wherein the cleaving base is selected from the group consisting of chemical base, ammonium hydroxide, electrochemically generated base, sodium hydroxide, potassium hydroxide, methylamine, and ethylamine and combinations thereof.

In an embodiment of the invention, a process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same, and cleaving at the base-labile cleaving site the oligomers from the surface using a cleaving base to provide a pool of cleaved oligomers, wherein the oligomers are synthesized in situ using electrochemical synthesis.

In an embodiment of the invention, a process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same, and cleaving at the base-labile cleaving site the oligomers from the surface using a cleaving base to provide a pool of cleaved oligomers, wherein the oligomers are synthesized in situ by a method selected from the group consisting of (i) printing reagents via ink jet or other printing technology and using regular phosphoramidite chemistry, (ii) maskless photo-generated acid controlled synthesis and using regular phosphoramidite chemistry, (iii) mask-directed parallel synthesis using photo-cleavage of photolabile protecting groups, and (iv) maskless parallel synthesis using photo-cleavage of photolabile protecting groups and digital photolithography.

In an embodiment of the invention, a pool of oligomers produced according to the process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same, and cleaving at the base-labile cleaving site the oligomers from the surface using a cleaving base to provide a pool of cleaved oligomers, wherein the oligomers are oligonucleotides having a 3' phosphate, wherein the pool comprises more than approximately 100 different oligonucleotides.

In an embodiment of the invention, a pool of oligomers produced according to the process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same, and cleaving at the base-labile cleaving site the oligomers from the surface using a cleaving base to provide a pool of cleaved oligomers, wherein the oligomers are oligonucleotides having a 3' hydroxyl, wherein the pool comprises more than approximately 100 different oligonucleotides.

In an embodiment of the invention, a process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same, and cleaving at the base-labile cleaving site the oligomers from the surface using a cleaving base to provide a pool of cleaved oligomers, wherein the surface has electrodes and each of the known locations are associated with one of the electrodes, wherein the electrodes are electronically addressable.

In an embodiment of the invention, a pool of oligomers produced according to the process of forming a microarray having base cleavable phosphoramidite linkers comprises providing a microarray having a surface with a plurality of known locations on the surface, wherein each location has a plurality of hydroxyl groups, wherein the density of the known locations is greater than approximately 100 per square centimeter on the surface and bonding a plurality of base cleavable phosphoramidite linkers to the plurality of hydroxyl groups directly or by using an intermediate chemical moiety attached to the hydroxyl groups to form a plurality of cleavable linkers at the plurality of known locations, wherein the cleavable linkers each have a linker hydroxyl group and a base-labile cleaving site, wherein the linker hydroxyl group is protected by a protecting group and the base-labile cleaving site is an ether linkage, further comprising synthesizing oligomers onto the linker hydroxyl groups to provide a microarray of oligomers, wherein the protecting group is removed from the linker hydroxyl groups before synthesizing the oligomers, wherein the oligomers at the known locations, as between different known locations, are different or the same, and cleaving at the base-labile cleaving site the oligomers from the surface using a cleaving base to provide a pool of cleaved oligomers, wherein the oligomers are oligonucleotides having a 3' hydroxyl, wherein the pool comprises more than approximately 100 different oligonucleotides, wherein the known locations are on the same surface as the electrodes, on an opposing surface to the electrodes, or on an overlayer over the electrodes.

In an embodiment of the invention, a microarray having base cleavable linkers comprises a microarray having a surface with a plurality of known locations on the surface, wherein each location has a plurality of hydroxyl groups, wherein the density of the known locations is greater than approximately 100 per square centimeter on the surface and a plurality of base cleavable linkers bonded to the plurality of hydroxyl groups to form a plurality of cleavable linkers at the plurality of known locations, wherein the cleavable linkers each have a linker hydroxyl group and a base-labile cleaving site.

We claim:
1. A process of forming a pool of oligomers comprising:
 (a) providing a microarray having a surface with a plurality of known locations on the surface, wherein each location has a plurality of hydroxyl surface bound species, wherein a plurality of hydroxyl surface bound species are bound to a plurality of electronically addressable electrodes;
 (b) bonding a plurality of monomers at the plurality of known locations on the surface to generate a spacer bearing subsequent hydroxyl surface bound species;
 (c) bonding a plurality of amine amidite linkers including a phosphorous moiety which forms a phosphorous-oxygen bond with the subsequent hydroxyl surface bound species to form a plurality of protected amine surface bound species, wherein the plurality of protected amine surface bound species include an acid labile protecting group;
 (d) generating acidic conditions to remove the protecting groups of step (c) and reacting a protected succinate nucleoside moiety therewith to form a plurality of protected succinate nucleoside bound species, wherein the plurality of protected succinate nucleoside bound species include an acid-labile group protecting its 5'OH;
 (e) turning on one or more of the plurality of electronically addressable electrodes to generate acidic conditions to remove protecting groups from a plurality of succinate nucleoside bound species in one or more known first locations selected from the plurality of known locations;
 (f) reacting a first protected monomer with at least the known first locations of step (e) to form a plurality of first protected monomer bound species, wherein the plurality of first protected monomer bound species include an acid-labile 5' protecting group;
 (g) turning on one or more of the plurality of electronically addressable electrodes to generate acidic conditions to remove the protecting groups from a second plurality of succinate nucleoside bound species in one or more known second locations selected from the plurality of known locations;
 (h) reacting a second protected monomer with the one or more known second locations to form a plurality of second protected monomer bound species, wherein the plurality of second protected monomer bound species include an acid-labile 5' protecting group;
 (i) turning on one or more of the plurality of electronically addressable electrodes to generate acidic conditions to remove the acid-labile 5' protecting group in one or more known third locations selected from the plurality of known locations;

(j) reacting a third protected monomer at the one or more known third locations, wherein the third protected monomer includes an acid-labile 5' protecting group;

(k) repeating steps (i) through (j) to generate a plurality of oligomers, wherein the plurality of oligomers differ as to their sequence as between different known locations; and (l) forming a pool of oligomers by introducing a cleaving base to cleave the succinate base-labile cleavage site of the plurality of oligomers.

2. The process of claim 1, wherein the pool of oligomers are selected from the group consisting of DNA, RNA and combinations thereof.

3. The process of claim 1, wherein the cleaving base is one or more compounds selected from the group consisting of chemical base, ammonium hydroxide, electrochemically generated base, sodium hydroxide, potassium hydroxide, methylamine, and ethylamine.

4. The process of claim 1, wherein the oligomers are synthesized in situ using electrochemical synthesis.

5. The process of claim 1, wherein the oligomers are synthesized in situ by a method selected from the group consisting of (i) printing reagents via ink jet or other printing technology and using regular phosphoramidite chemistry, (ii) maskless photo-generated acid controlled synthesis and using regular phosphoramidite chemistry, (iii) mask-directed parallel synthesis using photo-cleavage of photolabile protecting groups, and (iv) maskless parallel synthesis using photo-cleavage of photolabile protecting groups and digital photolithography.

6. The process of claim 1, wherein the pool of oligomers comprises more than approximately 100 different oligonucleotides.

7. The process of claim 1, wherein the first protected monomer includes a base-labile protecting group on the nucleobase.

8. The process of claim 1, further comprising wherein the cleaving base is electrochemically generated.

9. The process of claim 8, further comprising adding one or more compounds selected from the group consisting of ammonium hydroxide, sodium hydroxide, potassium hydroxide, methylamine, and ethylamine.

10. The process of claim 1, wherein an oligomer is added using electrochemical synthesis.

11. The process of claim 1, where the pool of oligomers have a free hydroxyl at the 3' position.

12. A process of forming a pool of oligomers comprising:

(a) providing a microarray having a surface with a plurality of known locations on the surface, where each location has a first plurality of hydroxyl surface bound species, where the first plurality of hydroxyl surface bound species are bound to a plurality of electronically addressable electrodes;

(b) bonding a plurality of monomers at the plurality of known locations on the surface to generate a spacer providing a second plurality of hydroxyl surface bound species;

(c) bonding a plurality of amine amidite linkers including a phosphorous moiety which forms a phosphorous-oxygen bond with the second plurality of hydroxyl surface bound species to form a plurality of protected amino surface bound species, where the plurality of protected amino surface bound species include an acid labile protecting group;

(d) turning on one or more of the plurality of electronically addressable electrodes to generate acidic conditions to remove the protecting groups from a plurality of amino bound species in at least one of the first locations of step (b) selected from the plurality of known locations;

(e) reacting a first protected succinate nucleoside moiety with the plurality of amino bound species of step (d) to form a first plurality of protected succinate nucleoside bound species, where the first plurality of protected succinate nucleoside bound species includes an acid-labile 5' protecting group;

(f) turning on one or more of the plurality of electronically addressable electrodes to generate acidic conditions to remove the protecting groups from a plurality of amino bound species in at least one location of step (e) selected from the plurality of known locations;

(g) reacting a second protected succinate nucleoside moiety with the plurality of amino bound species of step (c) to form a second plurality of protected succinate nucleoside bound species, where the second plurality of protected succinate nucleoside bound species include an acid-labile 5' protecting group, where the second plurality of protected succinate nucleoside bound species includes a succinate base-labile cleavage site;

(h) turning on one or more of a plurality of electronically addressable electrodes to generate acidic conditions to remove the protecting groups from a plurality of protected succinate nucleoside bound species in at least one location of step (g) selected from the plurality of known locations;

(i) bonding a plurality of protected monomers including a phosphorous moiety in at least one location of step (h), where the plurality of protected monomers include an acid-labile 5' protecting group;

(j) turning on one or more of the plurality of electronically addressable electrodes to generate acidic conditions to remove the protecting groups in at least one location of step (i) selected from the plurality of known locations and bonding a plurality of protected monomers including a phosphorous moiety at the one or more known fourth locations, where the plurality of protected monomers include an acid-labile 5' protecting group;

(k) repeating steps (h) through (j) to generate a plurality of oligomers, where the plurality of oligomers differ as to their sequence as between different known locations; and (l) forming a pool of oligomers by introducing a cleaving base to cleave the succinate base-labile cleavage site of the plurality of oligomers.

13. The process of claim 12, where the plurality of protected monomers includes a base-labile protecting group on the nucleobase.

14. The process of claim 12, where the pool of oligomers are selected from the group consisting of DNA, RNA, and combinations thereof.

15. The process of claim 12, further comprising where the cleaving base is electrochemically generated.

16. The process of claim 15, further comprising adding one or more compounds selected from the group consisting of ammonium hydroxide, sodium hydroxide, potassium hydroxide, methylamine, and ethylamine.

17. The process of claim 12, where the cleaving base is one or more compounds selected from the group consisting of ammonium hydroxide, sodium hydroxide, potassium hydroxide, methylamine, and ethylamine.

18. The process of claim 12, where an oligomer is added using electrochemical synthesis.

19. The process of claim 12, where the oligomers are synthesized in situ by a method selected from the group consisting of (i) printing reagents via ink jet or other printing technology and using regular phosphoramidite chemistry, (ii) maskless photo-generated acid controlled synthesis and using regular phosphoramidite chemistry, (iii) mask-directed parallel synthesis using photo-cleavage of photolabile protecting groups, and (iv) maskless parallel synthesis using photo-cleavage of photolabile protecting groups and digital photolithography.

20. The process of claim 12, where the pool of oligomers comprises more than approximately 100 different oligonucleotides.

21. The process of claim 12, where the pool of oligomers have a free hydroxyl at the 3' position.

* * * * *